United States Patent
Liao

(10) Patent No.: US 11,535,645 B2
(45) Date of Patent: Dec. 27, 2022

(54) 6-MERCAPTOPURINE NUCLEOSIDE ANALOGUES

(71) Applicant: Xibin Liao, Edison, NJ (US)

(72) Inventor: Xibin Liao, Edison, NJ (US)

( * ) Notice: Subject to any disclaimer, the term of this patent is extended or adjusted under 35 U.S.C. 154(b) by 16 days.

(21) Appl. No.: 17/285,462

(22) PCT Filed: Oct. 16, 2019

(86) PCT No.: PCT/US2019/056546
§ 371 (c)(1),
(2) Date: Apr. 14, 2021

(87) PCT Pub. No.: WO2020/081690
PCT Pub. Date: Apr. 23, 2020

(65) Prior Publication Data
US 2021/0380628 A1 Dec. 9, 2021

Related U.S. Application Data

(60) Provisional application No. 62/746,701, filed on Oct. 17, 2018.

(51) Int. Cl.
*C07H 19/207* (2006.01)
*C07H 19/213* (2006.01)

(52) U.S. Cl.
CPC ......... *C07H 19/207* (2013.01); *C07H 19/213* (2013.01)

(58) Field of Classification Search
None
See application file for complete search history.

(56) References Cited

U.S. PATENT DOCUMENTS

| | | | |
|---|---|---|---|
| 3,074,930 A | 1/1963 | Hitchings et al. | |
| 2012/0141491 A1* | 6/2012 | Dunn | A61K 31/519 424/141.1 |

FOREIGN PATENT DOCUMENTS

| | | |
|---|---|---|
| WO | 0190121 A2 | 11/2001 |
| WO | 2007010515 A1 | 1/2007 |
| WO | 2007027248 A2 | 3/2007 |
| WO | 2014168947 A2 | 10/2014 |

OTHER PUBLICATIONS

Wolff, Manfred E. "Burger's Medicinal Chemistry, 5ed, Part I", John Wiley & Sons, 1995, pp. 975-977. (Year: 1995).*
Banker, G.S. et al, "Modern Pharmaceutics, 3ed.", Marcel Dekker, New York, 1996, p. 596 (Year: 1996).*
Herbert et al., Journal of Biological Chemistry, vol. 273, No. 10, 1998, pp. 5557-5565. (Year: 1998).*
Pubmed Compound Summary for CID 15172122, US National Library of Medicine, Feb. 9, 2007, pp. 1-18.
Beltman et al., "Characterization of cyclic nucleotide phosphodiesterases with cyclic GMP analogs: Topology of the catalytic domains", Molecular Pharmacology, Feb. 1, 1995, vol. 47, pp. 330-339.
Pubmed Compound Summary for CID 127258074, US National Library of Medicine, Jun. 18, 2017, pp. 1-14.
Tanaka JC et al., "Photoreceptor channel activation by nucleotide derivative", Biochemistry, vol. 28, No. 8, Apr. 4, 2989, pp. 2776-2784.
Katharina Werner et al., "Quantification of cAMP and cGMP analogs in tact cells: pitfalls in enzyme Immunoassays for cyclic nucleotides" Naunyn-Schmiedeberg's archives of pharmacology, Springer, Berlin, DE, vol. 384, No. 2, Jun. 29, 2011, pp. 169-176.

* cited by examiner

*Primary Examiner* — Traviss C McIntosh, III
(74) *Attorney, Agent, or Firm* — SZDC Law P.C.

(57) ABSTRACT

A compound has the following formula (I) or formula (II), an isomer thereof, a tautomer thereof, a pharmaceutical acceptable solvate thereof, or a pharmaceutical acceptable prodrug thereof.

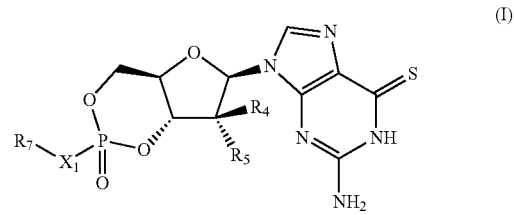

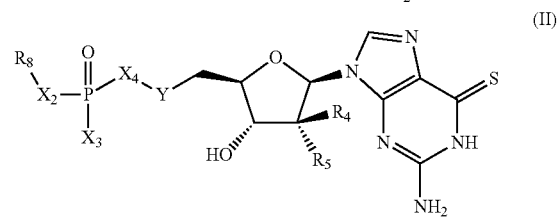

7 Claims, No Drawings

6-MERCAPTOPURINE NUCLEOSIDE ANALOGUES

The present application is the National Phase Application of PCT/US2019/056546, filed on Oct. 16, 2019, which claims priority to US Provisional Application Number 62/746,701, filed on Oct. 17, 2018, which is incorporated by reference for all purposes as if fully set forth herein.

FIELD OF THE INVENTION

The present invention relates to 6-mercaptopurine nucleoside analogues for treating various deceases, such as cancer and viral infections.

BACKGROUND OF THE INVENTION

Nucleoside analogues are effective in treating various diseases, such as cancer and viral infections like herpes simplex virus (HSV), human immunodeficiency virus (HIV), hepatitis B virus (HBV), and hepatitis C virus (HCV). Nucleoside analogues are also used to selectively target telomerase activity. Most normal cells do not have telomerase activities.

There are many nucleoside analogues drugs on the market to treat cancer and viral infections. After entering cells, the nucleoside analogues are activated by nucleoside and nucleotide kinases to form phosphorylated nucleoside analogues. The phosphorylated nucleoside analogues exert their therapeutic effects.

The nucleoside analogue drugs, however, have some shortcomings. The phosphorylation of the nucleoside analogues is often inefficient. The nucleoside analogues have poor oral bioavailability due to low intestinal permeability. Resistance has been developed to some nucleoside analogues. To overcome these limitations, there is a need to for efficient and bioavailable nucleoside analogues.

SUMMARY OF THE INVENTION

The present invention provides a compound having the following formula (I), an isomer thereof, a tautomer thereof, a pharmaceutical acceptable solvate thereof, or a pharmaceutical acceptable prodrug thereof.

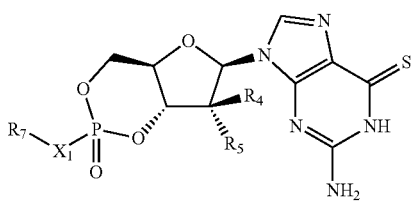

(I)

In formula (I), $X_1$ is —O— or —NH—; $R_7$ is —H, alkyl, alkyl substituted with one or more —OH or halo groups, alkenyl, alkenyl substituted with one or more —OH or halo groups, alkynyl, alkynyl substituted with one or more —OH or halo groups, cycloalkyl, cycloalkyl substituted with one or more —OH or halo groups, aryl, aryl substituted with one or more —OH, halo, —CN, —$NO_2$, alkyl, alkoxy, or haloalkyl groups, benzyl, benzyl substituted with one or more —OH, halo, —CN, —$NO_2$, alkyl, alkoxy, or haloalkyl groups, heteroaryl, heteroaryl substituted with one or more —OH, halo, —CN, —$NO_2$, alkyl, alkoxy, or haloalkyl groups, heterocyclyl, heterocyclic substituted with one or more —OH, halo, —CN, —$NO_2$, alkyl, alkoxy, or haloalkyl groups, —CH($CH_3$)COOCH($CH_3$)$_2$,

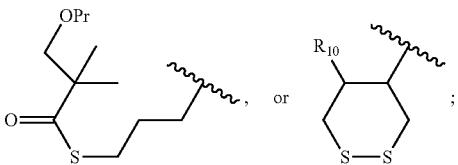

$R_4$ is —H, —OH, —$CH_3$, —Cl, —F, —$N_3$, —$OCH_3$, alkenyl, or alkynyl; $R_5$ is —H, —OH, —$CH_3$, —Cl, —F, —$N_3$, —$OCH_3$, alkenyl, or alkynyl; and $R_{10}$ is -L-M, wherein L is —O—, —O—$CH_2$—, —S—, —NH—, —CO—, —SO—, or —$CH_2$—, and M is alkyl, alkyl substituted with one or more —OH or halo groups, alkenyl, alkenyl substituted with one or more —OH or halo groups, alkynyl, alkynyl substituted with one or more —OH or halo groups, alkoxy, alkoxy substituted with one or more —OH or halo groups, cycloalkyl, cycloalkyl substituted with one or more —OH or halo groups, aryl, aryl substituted with one or more —OH, halo, —CN, —$NO_2$, alkyl, alkoxy, or haloalkyl groups, benzyl, benzyl substituted with one or more —OH, halo, —CN, —$NO_2$, alkyl, alkoxy, or haloalkyl groups, heteroaryl, heteroaryl substituted with one or more —OH, halo, —CN, —$NO_2$, alkyl, alkoxy, or haloalkyl groups, heterocyclyl, or heterocyclic substituted with one or more —OH, halo, —CN, —$NO_2$, alkyl, alkoxy, or haloalkyl groups.

In another embodiment, in formula (I), $X_1$ is —O—; $R_7$ is

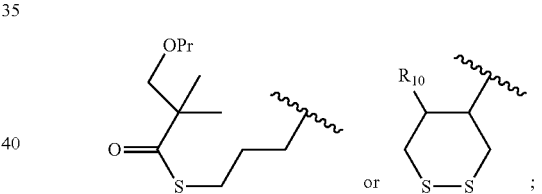

$R_4$ is —H; $R_5$ is —H; and $R_{10}$ is -L-M, wherein L is —O— or —O—$CH_2$—, and M is alkynyl, alkynyl substituted with one or more —OH or halo groups, aryl, aryl substituted with one or more —OH, halo, —CN, —$NO_2$, alkyl, alkoxy, or haloalkyl groups, benzyl, benzyl substituted with one or more —OH, halo, —CN, —$NO_2$, alkyl, alkoxy, or haloalkyl groups, heterocyclyl, or heterocyclic substituted with one or more —OH, halo, —CN, —$NO_2$, alkyl, alkoxy, or haloalkyl groups.

In another embodiment, the compound of formula (I) is selected from the group consisting of: 2-amino-9-((2S,4aR,6R,7aS)-2-(((4R,5R)-5-(benzyloxy)-1,2-dithian-4-yl)oxy)-2-oxidotetrahydro-4H-furo[3,2-d][1,3,2]dioxaphosphinin-6-yl)-1,9-dihydro-6H-purine-6-thione; 2-amino-9-((2S,4aR,6R,7aS)-2-(((4S,5S)-5-(benzyloxy)-1,2-dithian-4-yl)oxy)-2-oxidotetrahydro-4H-furo[3,2-d][1,3,2]dioxaphosphinin-6-yl)-1,9-dihydro-6H-purine-6-thione; 2-amino-9-((2R,4aR,6R,7aS)-2-(((4S,5S)-5-(benzyloxy)-1,2-dithian-4-yl)oxy)-2-oxidotetrahydro-4H-furo[3,2-d][1,3,2]dioxaphosphinin-6-yl)-1,9-dihydro-6H-purine-6-thione; 2-amino-9-((2R,4aR,6R,7aS)-2-(((4R,5R)-5-(benzyloxy)-1,2-dithian-4-yl)oxy)-2-oxidotetrahydro-4H-furo[3,2-d][1,3,2]dioxaphosphinin-6-yl)-1,9-dihydro-6H-purine-6-thione; S-(3-(((2R,4aR,6R,7aS)-6-(2-amino-6-thioxo-1,6-dihydro-9H-purin-9-yl)-2- oxidotetrahydro-4H-furo[3,2-d][1,3,2]dioxaphosphinin-2-yl)oxy)propyl) 2,2-dimethyl-3-propoxypropanethioate; S-(3-(((2S,4aR,6R,7aS)-6-(2-amino-6-thioxo-1,6-dihydro-9H-purin-9-yl)-2-oxidotetrahydro-4H-furo[3,2-d][1,3,2]dioxaphosphinin-2-yl)oxy)propyl) 2,2-dimethyl-3-propoxypropanethioate; 2-amino-9-((2S,4aR,6R,7aS)-2-(((4R,5R)-5-(benzyloxy)-1,2-dithian-4-yl)oxy)-2-sulfidotetrahydro-4H-furo[3,2-d][1,3,2]dioxaphosphinin-6-yl)-1,9-dihydro-6H-purine-6-thione; 2-amino-9-((2R,4aR,6R,7aS)-2-(((4R,5R)-5-((2-methylbenzyl)oxy)-1,2-dithian-4-yl)oxy)-2-oxidotetrahydro-4H-furo[3,2-d][1,3,2]dioxaphosphinin-6-yl)-1,9-dihydro-6H-purine-6-thione; 2-amino-9-((2R,4aR,6R,7aS)-2-oxido-2-(((4R,5R)-5-(prop-2-yn-1-yloxy)-1,2-dithian-4-yl)oxy)tetrahydro-4H-furo[3,2-d][1,3,2]dioxaphosphinin-6-yl)-1,9-dihydro-6H-purine-6-thione; 2-amino-9-((2R,4aR,6R,7aS)-2-(((4R,5R)-5-methoxy-1,2-dithian-4-yl)oxy)-2-oxidotetrahydro-4H-furo[3,2-d][1,3,2]dioxaphosphinin-6-yl)-1,9-dihydro-6H-purine-6-thione; and 2-amino-9-((2R,4aR,6R,7aS)-2-oxido-2-(((4R,5R)-5-(pyridin-4-ylmethoxy)-1,2-dithian-4-yl)oxy)tetrahydro-4H-furo[3,2-d][1,3,2]dioxaphosphinin-6-yl)-1,9-dihydro-6H-purine-6-thione.

In one embodiment, the present application provides a compound having the following formula (II), an isomer thereof, a tautomer thereof, a pharmaceutical acceptable solvate thereof, or a pharmaceutical acceptable prodrug thereof.

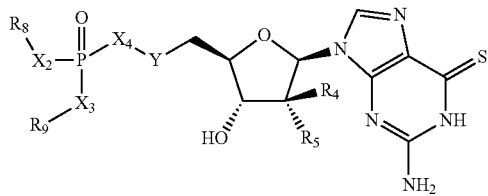
(II)

In formula (II), $X_2$ is —O— or —NH—; $X_3$ is —O— or —NH—; $X_4$ is —CH$_2$— or nil; Y is —O—, —S—, or —SO$_2$—; $R_8$ and $R_9$ are independently selected from the group consisting of —H, alkyl, alkyl substituted with one or more —OH or halo groups, alkenyl, alkenyl substituted with one or more —OH or halo groups, alkynyl, alkynyl substituted with one or more —OH or halo groups, cycloalkyl, cycloalkyl substituted with one or more —OH or halo groups, aryl, aryl substituted with one or more —OH, halo, —CN, —NO$_2$, alkyl, alkoxy, or haloalkyl groups, benzyl, benzyl substituted with one or more —OH, halo, —CN, —NO$_2$, alkyl, alkoxy, or haloalkyl groups, heteroaryl, heteroaryl substituted with one or more —OH, halo, —CN, —NO$_2$, alkyl, alkoxy, or haloalkyl groups, heterocyclyl, heterocyclic substituted with one or more —OH, halo, —CN, —NO$_2$, alkyl, alkoxy, or haloalkyl groups, —CH(CH$_3$)COOCH(CH$_3$)$_2$,

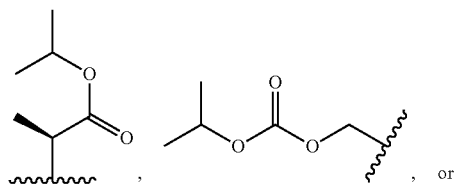

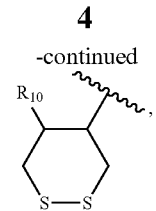

or $R_8$ and $R_9$ form a five-membered or six-membered heterocyclo ring or a five-membered or six-membered heterocyclo ring substituted with one or more —OH, halo, —CN, —NO$_2$, alkyl, alkoxy, benzyl, benzyl substituted with one or more —OH, halo, —CN, —NO$_2$, alkyl, alkoxy, or haloalkyl groups, or haloalkyl groups; $R_4$ is —H, —OH, —CH$_3$, —Cl, —F, —N$_3$, —OCH$_3$, alkenyl, or alkynyl; $R_5$ is —H, —OH, —CH$_3$, —Cl, —F, —N$_3$, —OCH$_3$, alkenyl, or alkynyl; and $R_{10}$ is -L-M, wherein L is —O—, —O—CH$_2$—, —S—, —NH—, —CO—, —SO—, or —CH$_2$—, and M is alkyl, alkyl substituted with one or more —OH or halo groups, alkenyl, alkenyl substituted with one or more —OH or halo groups, alkynyl, alkynyl substituted with one or more —OH or halo groups, alkoxy, alkoxy substituted with one or more —OH or halo groups, cycloalkyl, cycloalkyl substituted with one or more —OH or halo groups, aryl, aryl substituted with one or more —OH, halo, —CN, —NO$_2$, alkyl, alkoxy, or haloalkyl groups, benzyl, benzyl substituted with one or more —OH, halo, —CN, —NO$_2$, alkyl, alkoxy, or haloalkyl groups, heteroaryl, heteroaryl substituted with one or more —OH, halo, —CN, —NO$_2$, alkyl, alkoxy, or haloalkyl groups, heterocyclyl, or heterocyclic substituted with one or more —OH, halo, —CN, -NO$_2$, alkyl, alkoxy, or haloalkyl groups.

In another embodiment, in formula (II), $R_8$ and $R_9$ are independently selected from the group consisting of —H, alkyl, alkyl substituted with one or more —OH or halo groups, aryl, aryl substituted with one or more —OH, halo, —CN, —NO$_2$, alkyl, alkoxy, or haloalkyl groups, benzyl, benzyl substituted with one or more —OH, halo, —CN, —NO$_2$, alkyl, alkoxy, or haloalkyl groups, —CH(CH$_3$)COOCH(CH$_3$)$_2$, —COCH$_3$,

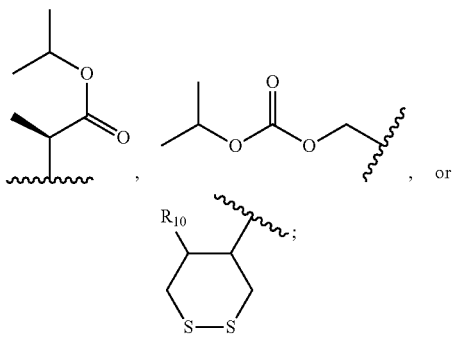

$R_4$ is —H; $R_5$ is —H; and $R_{10}$ is -L-M, wherein L is —O— or —O—CH$_2$—, and M is alkynyl, alkynyl substituted with one or more —OH or halo groups, aryl, aryl substituted with one or more —OH, halo, —CN, —NO$_2$, alkyl, alkoxy, or haloalkyl groups, benzyl, benzyl substituted with one or more —OH, halo, —CN, —NO$_2$, alkyl, alkoxy, or haloalkyl groups, heteroaryl, or heteroaryl substituted with one or more —OH, halo, —CN, —NO$_2$, alkyl, alkoxy, or haloalkyl groups.

In another embodiment, in formula (II), $R_8$ and $R_9$ form a five-membered or six-membered heterocyclo ring or a five-membered or six-membered heterocyclo ring substituted with one or more —OH, halo, —CN, —NO$_2$, alkyl, alkoxy, benzyl, benzyl substituted with one or more —OH, halo, —CN, —NO$_2$, alkyl, alkoxy, or haloalkyl groups, or haloalkyl groups; R$_4$ is —H; and R$_5$ is —H.

In another embodiment, the compound of formula (II) is selected from the group consisting of: isopropyl (((((2R,3S,5R)-5-(2-amino-6-mercapto-9H-purin-9-yl)-3-hydroxytetrahydrofuran-2-yl)methoxy)(phenoxy)phosphoryl)-L-alaninate; acetic (((2R,3S,5R)-5-(2-amino-6-mercapto-9H-purin-9-yl)-3-hydroxytetrahydrofuran-2-yl)methyl phenyl phosphoric) anhydride; isopropyl (((((2R,3S,5R)-5-(2-amino-6-mercapto-9H-purin-9-yl)-3-hydroxytetrahydrofuran-2-yl)methoxy)methyl)(phenoxy)phosphoryl)-L-alaninate; diphenyl ((((2R,3S,5R)-5-(2-amino-6-mercapto-9H-purin-9-yl)-3-hydroxytetrahydrofuran-2-yl)methoxy)methyl)phosphonate; 2-((((2R,3S,5R)-5-(2-amino-6-mercapto-9H-purin-9-yl)-3-hydroxytetrahydrofuran-2-yl)methoxy)methyl)-4-(3-chlorophenyl)-1,3,2-dioxaphosphinane 2-oxide; ((((((2R,3S,5R)-5-(2-amino-6-mercapto-9H-purin-9-yl)-3-hydroxytetrahydrofuran-2-yl)methoxy)methyl)phosphoryl)bis(oxy))bis(methylene) diisopropyl bis(carbonate); diethyl ((((2R,3S,5R)-5-(2-amino-6-mercapto-9H-purin-9-yl)-3-hydroxytetrahydrofuran-2-yl)methoxy)methyl)phosphonate; ((((2R,3S,5R)-5-(2-amino-6-mercapto-9H-purin-9-yl)-3-hydroxytetrahydrofuran-2-yl)methoxy)methyl)phosphonic acid; phenyl hydrogen ((((2R,3S,5R)-5-(2-amino-6-mercapto-9H-purin-9-yl)-3-hydroxytetrahydrofuran-2-yl)methoxy)methyl)phosphonate; (4R,5R)-5-(benzyloxy)-1,2-dithian-4-yl phenyl ((((2R,3S,5R)-5-(2-amino-6-mercapto-9H-purin-9-yl)-3-hydroxytetrahydrofuran-2-yl)methoxy)methyl)phosphonate; (4R,5R)-5-(benzyloxy)-1,2-dithian-4-yl P-((((2R,3S,5R)-5-(2-amino-6-mercapto-9H-purin-9-yl)-3-hydroxytetrahydrofuran-2-yl)methoxy)methyl)-N-benzylphosphonamidate; (4R, 5R)-5 -(prop-2-yn-1-yloxy)-1,2-dithian-4-yl P-((((2R,3S,5R)-5-(2-amino-6-mercapto-9H-purin-9-yl)-3-hydroxytetrahydrofuran-2-yl)methoxy)methyl)-N-benzylphosphonamidate; (4R,5R)-5-(benzyloxy)-1,2-dithian-4-yl (4-fluorophenyl) ((((2R,3S,5R)-5-(2-amino-6-mercapto-9H-purin-9-yl)-3-hydroxytetrahydrofuran-2-yl)methoxy)methyl) phosphonate; (4R,5R)-5-(benzyloxy)-1,2-dithian-4-yl (4-fluorophenyl) ((((2R,3S,5R)-5-(2-amino-6-mercapto-9H-purin-9-yl)-3-hydroxytetrahydrofuran-2-yl)methoxy) methyl)phosphonate; (4R,5R)-5-(benzyloxy)-1,2-dithian-4-yl (3-chlorophenyl) ((((2R,3S,5R)-5-(2-amino-6-mercapto-9H-purin-9-yl)-3-hydroxytetrahydrofuran-2-yl)methoxy) methyl)phosphonate; (4R,5R)-5-(benzyloxy)-1,2-dithian-4-yl o-tolyl ((((2R,3S,5R)-5-(2-amino-6-mercapto-9H-purin-9-yl)-3-hydroxytetrahydrofuran-2-yl)methoxy)methyl) phosphonate; ((((((2R,3S,5R)-5-(2-amino-6-mercapto-9H-purin-9-yl)-3-hydroxytetrahydrofuran-2-yl)methoxy)methyl)phosphoryl)bis(oxy))bis(methylene) bis(2,2-dimethylpropanoate); acetic (((2R,3S,5R)-5-(2-amino-6-mercapto-9H-purin-9-yl)-3-hydroxytetrahydrofuran-2-yl) methyl phosphoric) anhydride; and diethyl (((((2S,3S,5R)-5-(2-amino-6-mercapto-9H-purin-9-yl)-3-hydroxytetrahydrofuran-2-yl)methyl)thio)methyl) phosphonate.

DETAILED DESCRIPTION OF THE INVENTION

The present invention provides a compound having the following formula (I).

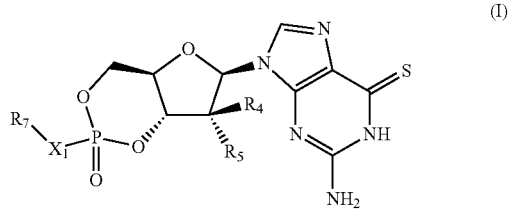

X$_1$, R$_7$, R$_4$, R$_5$ and R$_{10}$ are defined above.

The present invention also provides a compound having the following formula (II).

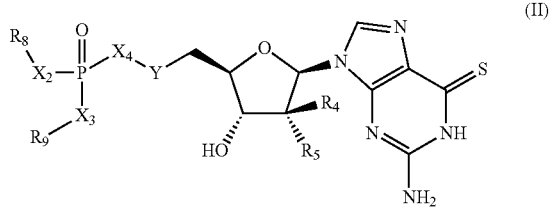

X$_2$, X$_3$, X$_4$, Y, R$_8$ and R$_9$ are defined above.

In formulas (I) and (II), P can be a chiral or achiral phosphorous atom. Compounds of formulas (I) and (II) may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration.

Alternatively, any stereoisomer of a compound of the general structural formulas (I) and (II) may be obtained by stereospecific synthesis using optically pure starting materials or reagents of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art.

Some of the compounds described herein contain olefinic double bonds, and, unless specified otherwise, are meant to include both E and Z geometric isomers.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are encompassed with compounds of structural formulas (I) and (II). An example of tautomers which are intended to be encompassed within the compounds of the present invention is illustrated below:

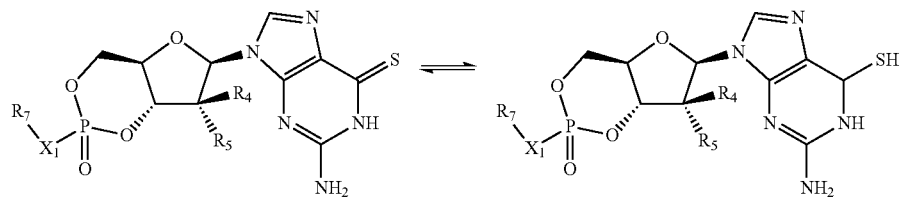

As used herein the following definitions are applicable.

"Alkyl," as well as other groups having the prefix "alk," such as alkoxy and alkanoyl, means carbon chains which may be linear or branched, and combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like. Where the specified number of carbon atoms permits, e.g., from $C_{3-10}$, the term alkyl also includes cycloalkyl groups, and combinations of linear or branched alkyl chains combined with cycloalkyl structures.

"Haloalkyl" refers to straight chain or branched alkyl groups, where some or all of the hydrogen atoms in these groups may be replaced by halogen atoms.

"Alkenyl" refers to straight or branched chain alkenes of two to twenty carbon atoms, or any number within this range. Examples of alkenyl groups include ethenyl, propenyl, butenyl, pentenyl, oleyl, and the like.

"Alkenyl" refers to straight or branched chain alkenes of two to twenty carbon atoms, or any number within this range. Examples of alkenyl groups include ethenyl, propenyl, butenyl, pentenyl, oleyl, and the like.

"Cycloalkyl" is a subset of "alkyl" and means a saturated carbocyclic ring having a specified number of carbon atoms. Examples of cycloalkyl include cyclopropyl, cyclobutyl, cyclopentyl, cyclohexyl, and cycloheptyl, and the like. A cycloalkyl group generally is monocyclic unless stated otherwise. Cycloalkyl groups are saturated unless otherwise defined.

"Aryl" refers to cyclic, aromatic hydrocarbon groups which have 1 to 3 aromatic rings, including phenyl and naphthyl. The aryl group may have fused thereto a second or third ring which is a heterocyclo, cycloalkyl, or heteroaryl ring, provided in that case the point of attachment will be to the aryl portion of the ring system.

"Heteroaryl" refers to an aromatic or partially aromatic heterocycle that contains at least one ring heteroatom selected from O, S and N. Heteroaryls thus include heteroaryls fused to other kinds of rings, such as aryls, cycloalkyls and heterocycles that are not aromatic. Examples of heteroaryl groups include: pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furyl, triazinyl, thienyl, pyrimidyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, benzodioxolyl, quinoxalinyl, purinyl, furazanyl, isobenzylfuranyl, benzimidazolyl, benzofuranyl, benzothienyl, quinolyl, indolyl, isoquinolyl, dibenzofuranyl, and the like.

"Heterocyclyl" or "heterocyclo ring" refers to fully saturated or partially unsaturated non-aromatic cyclic groups (for example, 4 to 7 membered monocyclic, 7 to 11 membered bicyclic, or 10 to 16 membered tricyclic ring systems) which have at least one heteroatom in at least one carbon atom-containing ring. Each ring of the heterocyclic group containing a heteroatom may have 1, 2, 3, or 4 heteroatoms selected from nitrogen atoms, oxygen atoms and/or sulfur atoms, where the nitrogen and/or sulfur heteroatoms may optionally be oxidized and the nitrogen heteroatoms may optionally be quaternized. A heterocyclo ring may have a carbon ring atom replaced with a carbonyl group (C=O), as illustrated above for cycloalkyl groups.

"Halo groups" refer to —F, —Cl, —Br, and —I.

The compounds of the present application may be prepared from known or readily prepared starting materials, following methods known to one skilled in the art of organic synthesis. Methods useful for making the compounds of Formula are set forth in the examples below and generalized in Schemes A, B, C below. Alternative synthetic pathways and analogous structures will be apparent to those skilled in the art of organic synthesis.

Scheme A shows a method useful for making nucleoside compounds of formula A4, which correspond to the compounds of Formula (II). In Scheme A, $R_1$, $R_2$, $R_3$, and $R_6$ are independently —H, alkyl, alkenyl, cycloalkyl, unsubstituted or substituted heteroaryl, substitute or substituted aryl; and $R_4$ and $R_5$ are independently —H, —OH, —CH$_3$, —Cl, —F, —N$_3$, —OCH$_3$, alkenyl, or alkynyl.

Scheme A

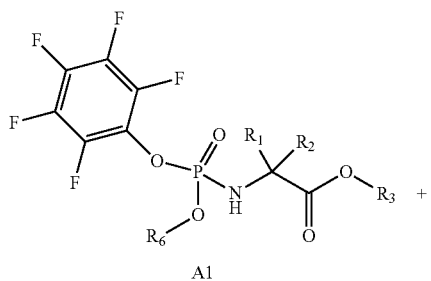

A1

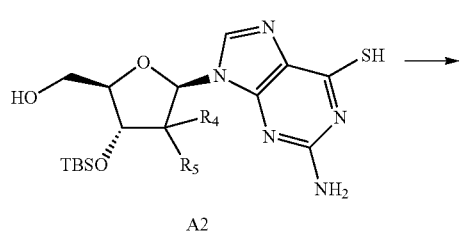

A2

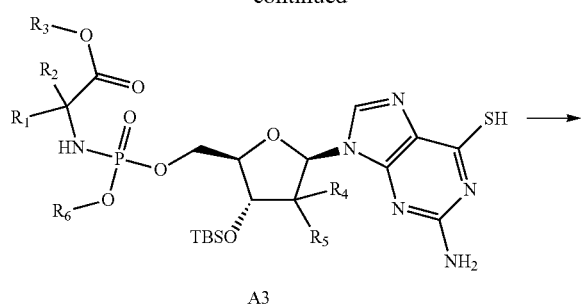

A3

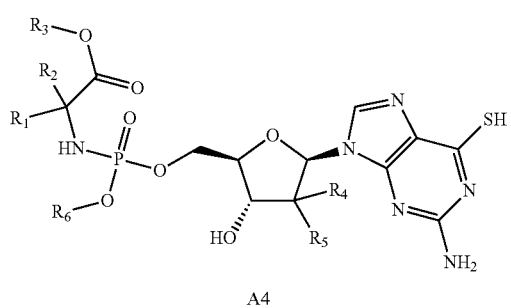

A4

Compounds of type A1 can be reacted with A2 to provide A3, then following TBS deprotection to provide compounds type A4.

Scheme B shows a method useful for making nucleoside compounds of formula B4, which correspond to the compounds of Formula (I). In Scheme B, $R_{10}$, $R_4$ and $R_5$ have the same definition as $R_{10}$, $R_4$ and $R_5$ in formula (II).

Scheme B

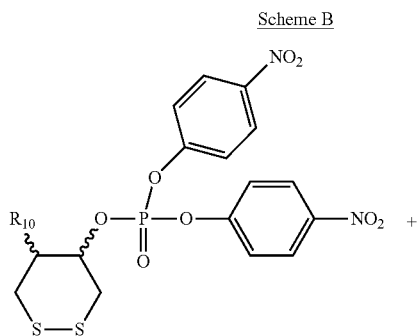

B1

B2

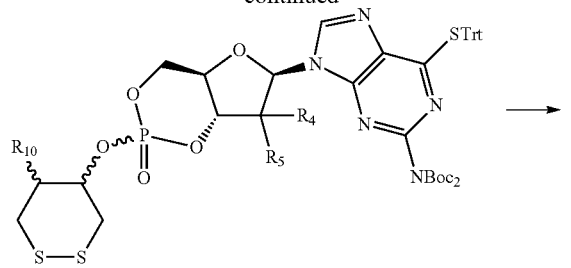

B3

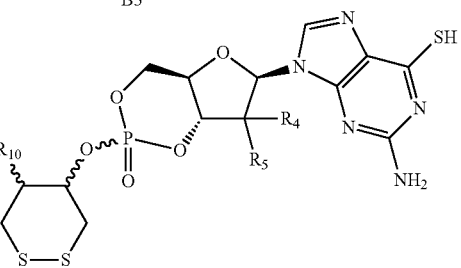

B4

Compounds of type B1 can be reacted with B2 to provide B3, then following protection group was removed to provide compounds type B4.

Scheme C shows a method useful for making nucleoside compounds of formula C4 and C5, which correspond to the compounds of Formula (II). In formula C4 and C5, $R_1$, $R_2$ are independently —H, alkyl, alkenyl, cycloalkyl, unsubstituted or substituted heteroaryl, unsubstituted, substituted aryl or form an substituted or substituted five-membered or six-membered heterocyclo rings and $R_4$ and $R_5$ are independently —H, —OH, —CH$_3$, —Cl, —F, —N$_3$, —OCH$_3$, alkenyl, or alkynyl.

Scheme C

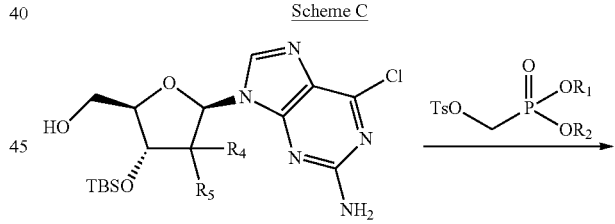

C1

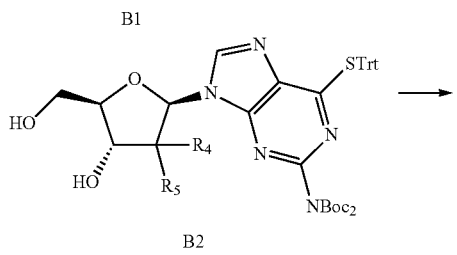

C2

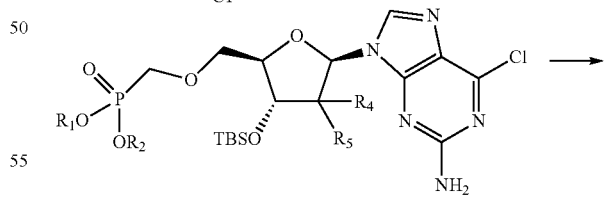

C3

-continued

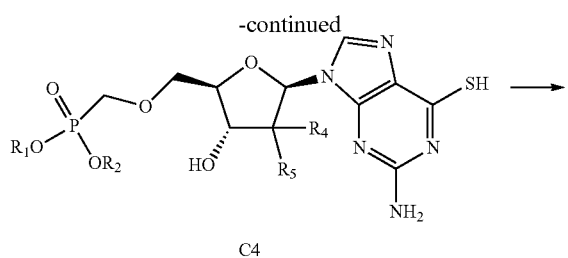

C4

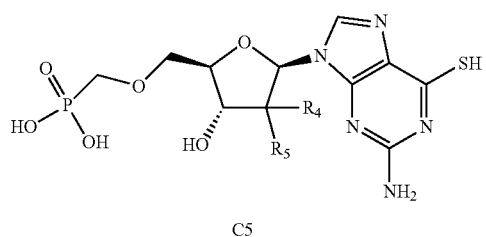

C5

Compounds of type C1 can be reacted with TsOCH$_2$P(O)OR$_1$OR$_2$ to provide C2, then convert the C1 to SH as C3, following protection group was removed to provide compounds type C4, further deprotect group R$_1$ and R$_2$ to provide compounds type C5.

General Procedures:

Preparative thin layer chromatography (PTLC) was performed on 20×20 cm plates (500 micron thick silica gel). Silica gel chromatography was performed on a Biotage Horizon flash chromatography system.

$^1$H and $^{31}$P NMR spectra were recorded on a Bruker Ascend™ 400 spectrometer at 400 MHz at 298° K., and the chemical shifts are given in parts per million (ppm) referenced to the residual proton signal of the deuterated solvents: CHCl$_3$ at δ=7.26 ppm and CH3OH or CH3OD at δ=3.30 ppm.

LCMS spectra were taken on an Agilent Technologies 1260 Infinity or 6120 Quadrupole spectrometer. The mobile phase for the LC was acetontrile (A) and water (B) with 0.01% formic acid, and the eluent gradient was from 5-95% A in 6.0 min, 60-95% A in 5.0 min, 80-100% A in 5.0 min and 85-100% A in 10 min using a SBC18 50 mm×4.6 mm×2.7 μm capillary column.

Mass spectra (MS) were measured by electrospray ion-mass spectroscopy (ESI). All temperatures are degrees Celsius unless otherwise noted.

Analytical HPLC mass spectrometry conditions:
LC1: Column: SB-C18 50 mm×4.6 mm×2.7 p,m
    Temperature: 5020 C.
    Eluent: 5:95 v/v acetonitrile/water+0.01% formic acid in 6 min.
    Flow Rate: 1.5 mL/min, Injection 5 μL
    Detection: PDA, 200-600 nm
    MS: mass range 150-750 amu; positive ion electrospray ionization
LC2: Column: SB-C18 50 mm×4.6 mm×2.7 μm
    Temperature: 5020 C.
    Eluent: 5:95 to 95:5 v/v acetonitrile/water+0.05% TFA over 3.00 min.
    Flow Rate: 1.5 mL/min, Injection 5 μL
    Detection: PDA, 200-600 nm
    MS: mass range 150-750 amu; positive ion electrospray ionization
LC3: Column: SB-C18 50 mm×4.6 mm×2.7 μm
    Temperature: 5020 C.
    Eluent: 10:90 to 98:2 v/v acetonitrile/water+0.05% TFA over 3.75 min.
    Flow Rate: 1.0 mL/min, Injection 10 μL
    Detection: PDA, 200-600 nm
    MS: mass range 150-750 amu; positive ion electrospray ionization The following abbreviations are used in the Examples, the Schemes, and the Tables: AcOH=acetic acid; Aq=aqueous; Alk=alkyl; Ar=aryl; Boc=tert-butyloxycarbonyl; br=broad singlet; CH$_2$Cl$_2$ =dichloromethane; d=doublet; dd=doublet of doublets; DBU=1,8-diazabicyclo[5.4.0]undec-7-ene; DCM=dichloromethane; DMA=4-dimethylaminopyridine; DMF=N,N-dimethylformamide; DMSO=dimethyl sulfoxide; EA=ethyl acetate; EDCI=1-ethyl-3-(3-dimethylaminopropyl)carbodiimide hydrochloride; ESI=electrospray ionization; Et=ethyl; Et$_3$N=triethylamine; EtOAc=ethyl acetate; EtOH=ethyl alcohol; h=hours; HPLC=high-performance liquid chromatography; HOAc=acetic acid; LiOH=lithium hydroxide; m=multiplet; Me=methyl; MeCN=acetonitrile; MeOH=methyl alcohol; MgSO$_4$=magnesium sulfate; min=minutes; MS=mass spectroscopy; NaCl=sodium chloride; NaOH=sodium hydroxide; Na$_2$SO$_4$=sodium sulfate; NMI=N-methylimidazole; NMR=nuclear magnetic resonance spectroscopy; PE=petroleum ether; PG=protecting group; Ph=phenyl; q=quartet; rt=room temperature; s=singlet; t=triplet; TBME=t-butyl dimethyl ether TFA=trifluoroacetic acid; THF=tetrahydrofuran; Ts=p-toluenesulfonyl (tosyl).

The Examples below provide illustrations of the conditions used for the preparation of the compounds of the present invention. The Examples provided are not intended to be limitations on the scope of the instant invention in any way, and they should not be so construed. Those skilled in the art of nucleoside and nucleotide synthesis will readily appreciate that known variations of the conditions and processes of the following preparative procedures can be used to prepare these and other compounds of the present invention.

EXAMPLE 1

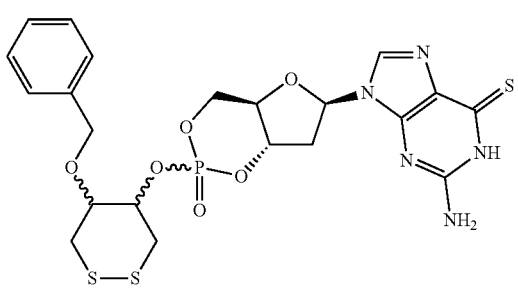

2-Amino-9-[2-(5-benzyloxy-[1,2]dithian-4-yloxy)-2-oxo-tetrahydro-2l5-furo[3,2-d][1,3,2]-dioxaphosphinin-6-yl]-1,9-dihydro-purine-6-thione

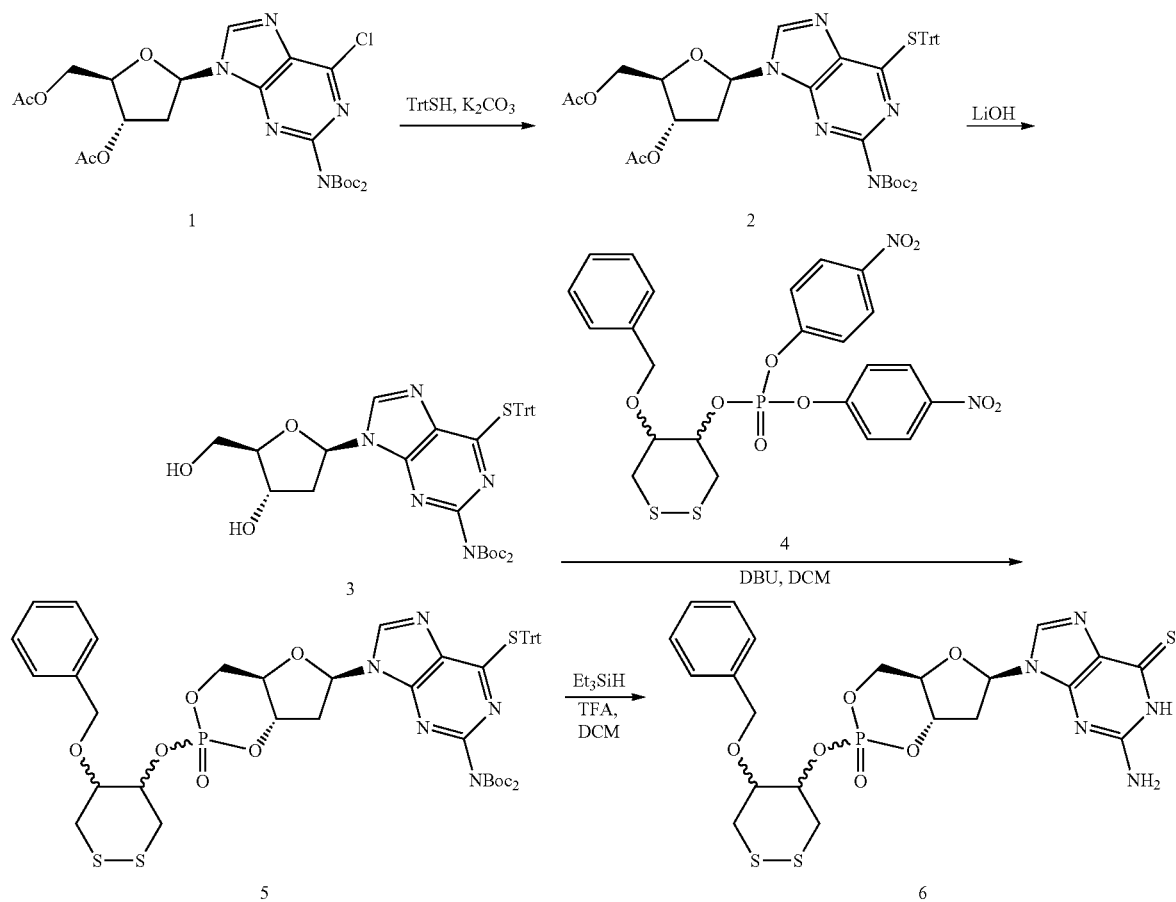

Step 1: Intermediate 2

A mixture of 1 (15.2 g, 26.7 mmol), triphenylmethyl mercaptan (11.1 g, 40.0 mmol) and K$_2$CO$_3$ (7.4 g, 53.3 mmol) in DMF (91 mL) was heated at 80 20 C. for 3 hours. The reaction mixture was cooled and poured into cold water. The resulting mixture was extracted with EtOAc twice. The combined organic layers were washed with water, brine and concentrated under reduced pressure. The residue was purified by column chromatography (PE/EtOAc=3/1-5/3) to give 2 (12.2 g, white amorphous solid, 56.5%).

$^1$H NMR (400 MHz, DMSO-d$_6$) δ 8.69 (1H, s), 7.29-7.20 (15H, m), 6.34 (1H, t, J=6.8 Hz), 5.36-5.33 (1H, m), 4.28-4.21 (2H, m), 4.15-4.08 (1H, m), 3.12-3.05 (1H, m), 2.58-2.52 (1H, m), 2.06 (3H, s), 1.96 (3H, s), 1.30 (18H, s).

Step 2: Intermediate 3

To a solution of 2 (12.2 g, 15.1 mmol) in THF (125 mL) was added a solution of LiOH.H$_2$O (3.16 g, 75.3 mmol) in water (25 mL). The reaction was stirred at room temperature overnight before poured into water. The resulting mixture was extracted with EtOAc twice. The combined organic layers were washed with brine, dried over Na$_2$SO$_4$ and concentrated under reduced pressure. The residue was suspended in tert-butyl methyl ether (80 mL) and stirred vigorously for 30 minutes. The slurry was filtered and washed with tert-butyl methyl ether (40 mL). The filter cake was collected and dried under reduced pressure to give 3 (9.4 g, white solid, 86.2%).

$^1$H NMR (400 MHz, DMSO-d$_6$) δ 8.68 (1H, s), 7.32-7.19 (15H, m), 6.29 (1H, t, J=6.8 Hz), 5.32 (1H, d, J=3.6 Hz), 4.92 (1H, brs), 4.41-4.35 (1H, m), 3.86-3.82 (1H, m), 3.59-3.43 (2H, m), 2.70-2.64 (1H, m), 2.32-2.26 (1H, m), 1.30 (18H, s).

Step 3: Intermediate 5

To the above reaction solution of 3 was added 4 (3369 mg, 4.64 mmol) and DBU (1882 mg, 12.4 mmol). The reaction was stirred at room temperature for 2 hours and then heated at 44 20 C. overnight. Most of the solvent was removed by evaporation. The residue was directly purified by column chromatography (PE/EtOAc=3/2-4/5) to give 5 (520 mg, yellowish amorphous solid, 16.6% two steps).

Step 4: Final Compound 6

To a solution of 5 (790 mg, 0.781 mmol) and triethylsilane (454 mg, 3.9 mmol) in DCM (10 mL) was added TFA (8 mL). The reaction was stirred at room temperature for 2 hours before concentrated under reduced pressure. The residue was azeotroped with DCM twice. The resulting residue was purified by column chromatography (DCM/MeOH=50/1-33/1-25/1) to give crude product. The crude product was suspended in MeOH (4 mL) and stirred for 30 minutes. The slurry was filtered and washed with MeOH (2 mL). The filter cake was collected and dried under reduced pressure to give 6 (101.4 mg, white solid, 22.8%).

LCMS: for $C_{21}H_{24}N_5O_6PS_3$, calculated 569.1, found 570.2 [M+H]$^+$. $^1$H NMR (400 MHz, DMSO-d$_6$) δ 12.03, 12.01 (1H, s), 8.20, 8.06 (1H, s, ratio 1:2), 7.39-7.11 (5H, m), 6.87, 6.82 (1H, brs), 6.27-6.20 (1H, m), 5.06-4.99, 4.92-4.85 (1H, m), 4.73-4.26 (5H, m), 4.02-3.93 (1H, m), 3.78-3.72 (1H, m), 3.61-3.42 (2H, m), 3.26-3.17 (1H, m), 3.01-2.94 (1H, m), 2.87-2.59, 2.35-2.28 (2H, m).

EXAMPLES 2-13

The compounds in Table 1 can be prepared by the same method as described in Examples 1.

TABLE 1

Compounds of Examples 2-12

| Ex. | Structure | MS | Name |
|---|---|---|---|
| 2 | 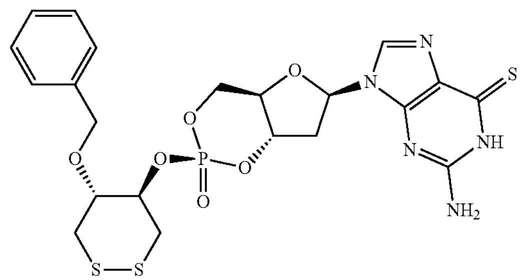 [SMILES: Nc1nc2c(ncn2[C@H]2C[C@@H]3O[P@@](=O)(O[C@H]4CSSC[C@@H]4OCc4ccccc4)OC[C@H]3O2)c(=S)[nH]1] | 569.06 | 2-amino-9-((2S,4aR,6R,7aS)-2-(((4R,5R)-5-(benzyloxy)-1,2-dithian-4-yl)oxy)-2-oxidotetrahydro-4H-furo[3,2-d][1,3,2]dioxaphosphinin-6-yl)-1,9-dihydro-6H-purine-6-thione |
| 3 | 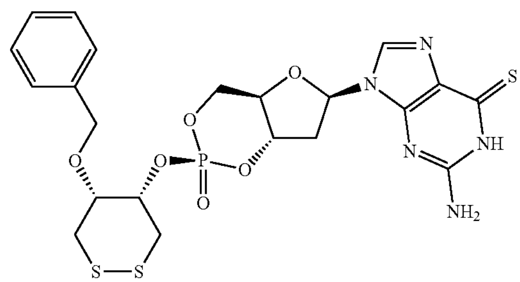 [SMILES: Nc1nc2c(ncn2[C@H]2C[C@@H]3O[P@@](=O)(O[C@@H]4CSSC[C@@H]4OCc4ccccc4)OC[C@H]3O2)c(=S)[nH]1] | 569.06 | 2-amino-9-((2S,4aR,6R,7aS)-2-(((4S,5S)-5-(benzyloxy)-1,2-dithian-4-yl)oxy)-2-oxidotetrahydro-4H-furo[3,2-d][1,3,2]dioxaphosphinin-6-yl)-1,9-dihydro-6H-purine-6-thione |
| 4 | 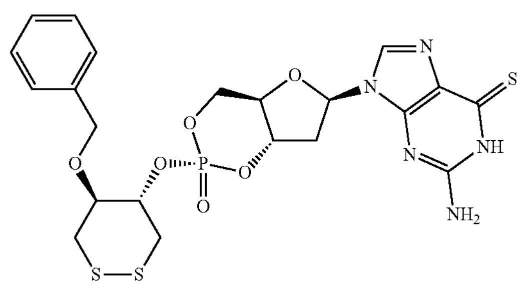 [SMILES: Nc1nc2c(ncn2[C@H]2C[C@@H]3O[P@](=O)(O[C@@H]4CSSC[C@H]4OCc4ccccc4)OC[C@H]3O2)c(=S)[nH]1] | 569.06 | 2-amino-9-((2R,4aR,6R,7aS)-2-(((4S,5S)-5-(benzyloxy)-1,2-dithian-4-yl)oxy)-2-oxidotetrahydro-4H-furo[3,2-d][1,3,2]dioxaphosphinin-6-yl)-1,9-dihydro-6H-purine-6-thione |
| 5 | 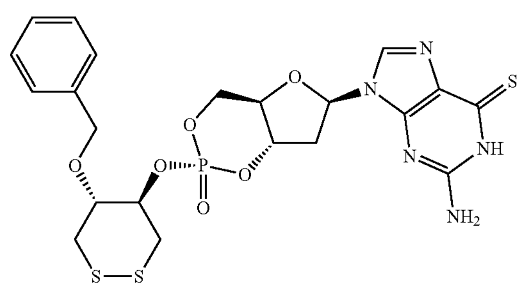 [SMILES: Nc1nc2c(ncn2[C@H]2C[C@@H]3O[P@](=O)(O[C@H]4CSSC[C@@H]4OCc4ccccc4)OC[C@H]3O2)c(=S)[nH]1] | 569.06 | 2-amino-9-((2R,4aR,6R,7aS)-2-(((4R,5R)-5-(benzyloxy)-1,2-dithian-4-yl)oxy)-2-oxidotetrahydro-4H-furo[3,2-d][1,3,2]dioxaphosphinin-6-yl)-1,9-dihydro-6H-purine-6-thione |
| 6 | 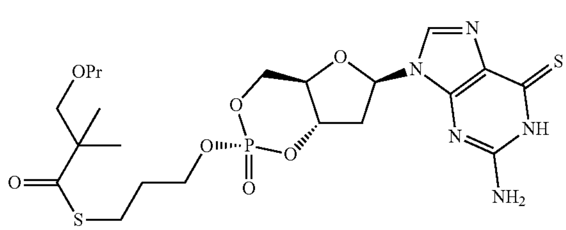 | 561.15 | S-(3-(((2R,4aR,6R,7aS)-6-(2-amino-6-thioxo-1,6-dihydro-9H-purin-9-yl)-2-oxidotetrahydro-4H-furo[3,2-d][1,3,2]dioxaphosphinin-2-yl)oxy)propyl) 2,2-dimethyl-3-propoxypropanethioate |

TABLE 1-continued

Compounds of Examples 2-12

| Ex. | Structure | MS | Name |
|---|---|---|---|
| 7 | 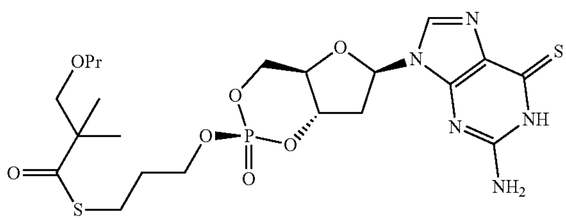 | 561.15 | S-(3-(((2S,4aR,6R,7aS)-6-(2-amino-6-thioxo-1,6-dihydro-9H-purin-9-yl)-2-oxidotetrahydro-4H-furo[3,2-d][1,3,2]dioxaphosphinin-2-yl)oxy)propyl) 2,2-dimethyl-3-propoxypropanethioate |
| 8 | 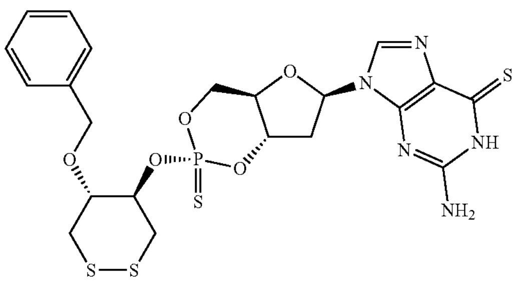 [SMILES: Nc1nc2c(ncn2[C@H]2C[C@@H]3O[P@](=S)(O[C@H]4CSSC[C@@H]4OCc4ccccc4)OC[C@H]3O2)c(=S)[nH]1] | 585.04 | 2-amino-9-((2S,4aR,6R,7aS)-2-(((4R,5R)-5-(benzyloxy)-1,2-dithian-4-yl)oxy)-2-sulfidotetrahydro-4H-furo[3,2-d][1,3,2]dioxaphosphinin-6-yl)-1,9-dihydro-6H-purine-6-thione |
| 9 | 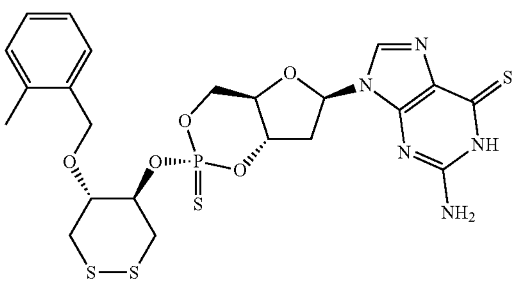 [SMILES: Cc1ccccc1CO[C@H]1CSSC[C@@H]1O[P@]1(=S)OC[C@H]2O[C@@H](n3cnc4c(=S)[nH]c(N)nc43)C[C@@H]2O1] | 583.08 | 2-amino-9-((2R,4aR,6R,7aS)-2-(((4R,5R)-5-((2-methylbenzyl)oxy)-1,2-dithian-4-yl)oxy)-2-oxidotetrahydro-4H-furo[3,2-d][1,3,2]dioxaphosphinin-6-yl)-1,9-dihydro-6H-purine-6-thione |
| 10 | 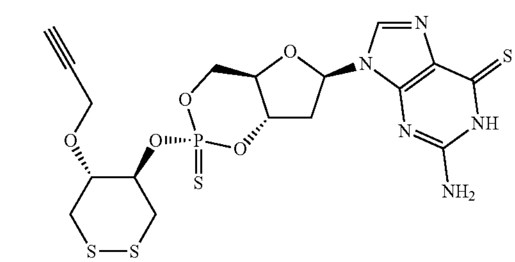 [SMILES: C#CCO[C@H]1CSSC[C@@H]1O[P@]1(=S)OC[C@H]2O[C@@H](n3cnc4c(=S)[nH]c(N)nc43)C[C@@H]2O1] | 517.03 | 2-amino-9-((2R,4aR,6R,7aS)-2-oxido-2-(((4R,5R)-5-(prop-2-yn-1-yloxy)-1,2-dithian-4-yl)oxy)tetrahydro-4H-furo[3,2-d][1,3,2]dioxaphosphinin-6-yl)-1,9-dihydro-6H-purine-6-thione |
| 11 | 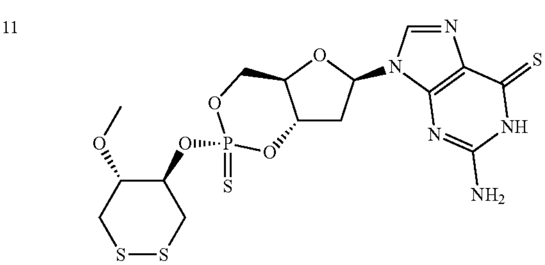 | 493.03 | 2-amino-9-((2R,4aR,6R,7aS)-2-oxido-2-5-methoxy-1,2-dithian-4-yl)oxy)-2-oxidotetrahydro-4H-furo[3,2-d][1,3,2]dioxaphosphinin-6-yl)-1,9-dihydro-6H-purine-6-thione |

TABLE 1-continued

Compounds of Examples 2-12

| Ex. | Structure | MS | Name |
|---|---|---|---|
| 12 | 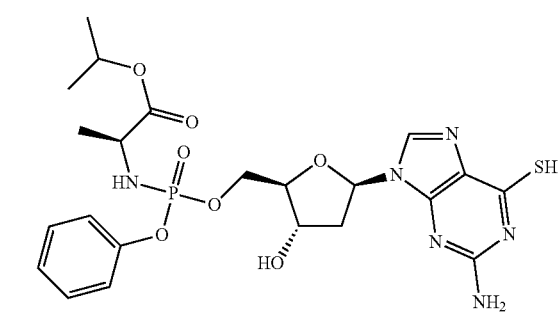 [SMILES: CC(C)OC(=O)[C@H](C)NP(=O)(OC[C@H]1O[C@@H](n2cnc3c(S)nc(N)nc32)C[C@@H]1O)Oc1ccccc1] | 570.06 | 2-amino-9-((2R,4aR,6R,7aS)-2-oxido-2-(((4R,5R)-5-(pyridin-4-ylmethoxy)-1,2-dithian-4-yl)oxy)tetrahydro-4H-furo[3,2-d][1,3,2]dioxaphosphinin-6-yl)-1,9-dihydro-6H-purine-6-thione |

EXAMPLE 13

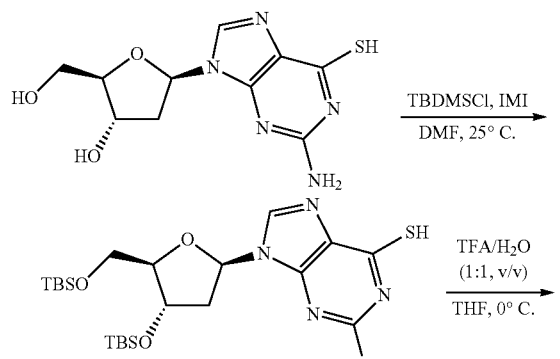

2-{[5-(2-Amino-6-mercapto-purin-9-yl)-3-hydroxy-tetrahydro-furan-2-ylmethoxy]-phenoxy-phosphorylamino}-propionic acid isopropyl ester

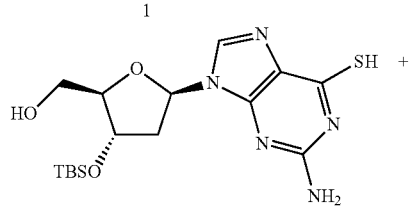

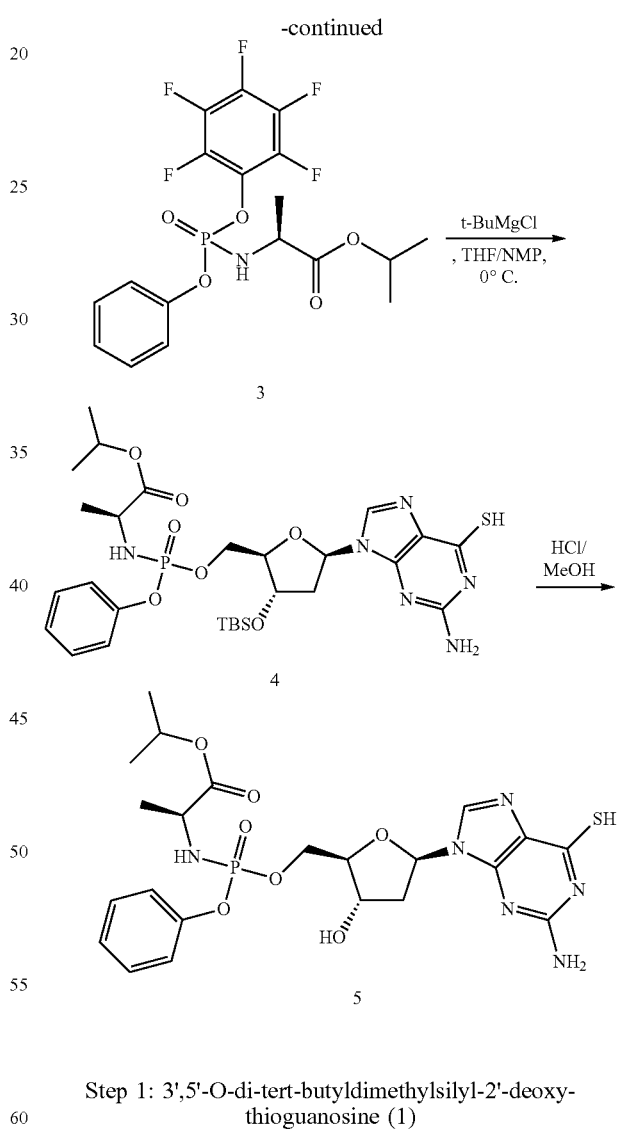

Step 1: 3',5'-O-di-tert-butyldimethylsilyl-2'-deoxy-thioguanosine (1)

To a solution of 2'-deoxythioguanosine (2.3 g, 8.13 mmol) and imidazole (3.65 g, 53.66 mmol) in 15 ml of anhydrous DMF was added 3.90 g (26.0 mmol) of tert-butyldimethylsilyl chloride (TBDMS-Cl). The reaction mixture was stirred at room temperature for 20 h. The resulting mixture was poured into water (100 mL). The precipitate was collected by filtration, rinsed with cooled mixture of ethanol and water (1:2), dried under reduced pressure to give 3.6 g title compound 1 as a gray solid (Yield 85%).

LC-MS: (ES, m/z): [M+H]+=512. $^1$H NMR (400 MHz, DMSO) δ 12.01 (s, 1H), 8.11 (s, 1H), 6.87 (s, 2H), 6.14 (t, J=6.5 Hz, 1H), 4.52 (s, 1H), 3.85 (s, 1H), 3.79-3.66 (m, 2H), 2.73-2.63 (m, 1H), 2.29 (dd, J=7.5, 3.9 Hz, 1H), 0.91 (d, J=4.6 Hz, 18H), 0.13 (s, 6H), 0.08 (s, 6H).

Step 2: 3'-O-tert-butyldimethylsilyl-5'-hydroxy-2'-deoxythioguanosine (2)

To a stirred solution of 1 (1.05 g, 1.96 mmol) in tetrahydrofuran (40 mL) was added TFA-H$_2$O (10 mL, 1:1 v/v) at 020 C. The reaction mixture was stirred at 020 C. for 2 hours. Saturated sodium bicarbonate solution was added to neutralize to pH~8. The solid was filtered, washed with cooled water, dried under reduced pressure to give product 2 (0.67 g, yield 84%) as a light gray powder.

LC-MS: (ES, m/z): [M+H]$^+$=398. $^1$H NMR (400 MHz, DMSO) δ 11.95 (s, 1H), 8.08 (s, 1H), 6.67 (s, 2H), 6.10 (t, J=6.7 Hz, 1H), 5.07 (s, 1H), 4.51 (s, 1H), 3.81 (s, 1H), 3.51 (d, J=8.6 Hz, 2H), 2.70-2.59 (m, 1H), 2.20 (d, J=9.0 Hz, 1H), 0.89 (s, 9H), 0.10 (s, 6H).

Step 3: Intermediate 4

To a stirred solution of protected 2'-deoxythioguanosine (2, 0.81 g, 2.05 mmol) in dry THF-NMP (20 mL, 1:1 v/v) was added a 1.0 M solution of tert-butylmagnesium chloride in THF (4.5 mL, 4.51 mmol) dropwise at room temperature. The white suspension was stirred at this temperature for 30 min, and a solution of commercial phosphate 3, (1.1 g, 2.45 mmol) in THF was added. The mixture was stirred at this temperature overnight. The reaction mixture was quenched with saturated NH$_4$Cl (aq) and extracted with ethyl acetate. The organic layers were combined, washed with brine, and dried over anhydrous Na$_2$SO$_4$. The solvent was removed under reduced pressure. The crude product was purified by column chromatography eluting with dichloromethane/methanol (20:1) to give the title compound 4 (0.75 g, yield 55%).

LC-MS: (ES, m/z): [M+H]$^+$=667. $^1$H NMR (400 MHz, DMSO) δ 11.98 (s, 1H), 8.10 (s, 1H), 7.36 (t, J=7.8 Hz, 2H), 7.18 (dd, J=15.3, 7.7 Hz, 3H), 6.82 (br, 2H), 6.13 (t, J=6.9 Hz, 1H), 6.06 (dd, J=12.8, 10.3 Hz, 1H), 4.83 (dt, J=12.5, 6.3 Hz, 1H), 4.52 (s, 1H), 4.23-4.14 (m, 1H), 4.07-3.95 (m, 2H), 3.77 (dd, J=17.2, 10.0 Hz, 1H), 3.17 (d, J=5.1 Hz, 1H), 2.75-2.61 (m, 1H), 2.25 (dd, J=12.0, 4.8 Hz, 1H), 1.20 (d, J=7.0 Hz, 3H), 1.16-1.08 (m, 6H), 0.87 (s, 9H), 0.08 (s, 6H). $^{31}$P NMR (400 MHz, DMSO) δ 3.70.

Step 4: 2-{[5-(2-Amino-6-mercapto-purin-9-yl)-3-hydroxy-tetrahydro-furan-2-ylmethoxy]-phenoxy-phosphorylamino}-propionic acid isopropyl ester (5)

20 mL fresh hydrogen chloride in methanol (prepared from addition of 5 mL acetyl chloride to 500 mL dry methanol) was added to the corresponding phosphoramidate 4 at room temperature. The reaction was stirred for 40 hours and then quenched with saturated aqueous sodium acetate. The resulting mixture was extracted with dichloromethane. The organic layers were combined, washed with brine, and dried over anhydrous Na$_2$SO$_4$. The solvent was removed under reduced pressure and the crude product was purified by Prep-TLC to give final product 5 (40 mg, yield 24%).

LC-MS: (ES, m/z): [M+H]$^+$=553. $^1$H NMR (400 MHz, DMSO) δ 11.96 (s, 1H), 8.04 (s, 1H), 7.36 (t, J=7.4 Hz, 2H), 7.18 (dd, J=16.6, 7.6 Hz, 3H), 6.81 (s, 2H), 6.14 (t, J=6.4 Hz, 1H), 6.00 (t, J=11.5 Hz, 1H), 5.44 (d, J=2.8 Hz, 1H), 4.89-4.77 (m, 1H), 4.38 (s, 1H), 4.19 (d, J=4.5 Hz, 1H), 4.03 (dd, J=20.3, 9.5 Hz, 2H), 3.78 (d, J=7.1 Hz, 1H), 2.56 (d, J=6.6 Hz, 1H), 2.26 (s, 1H), 1.20 (d, J=6.7 Hz, 3H), 1.13 (d, J=3.3 Hz, 6H). $^{31}$P NMR (400 MHz, DMSO) δ 3.80.

EXAMPLE 14

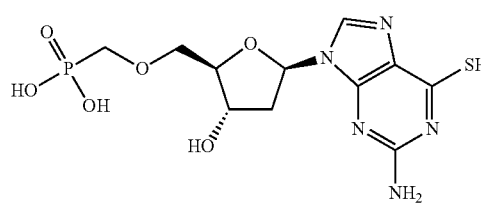

((((2R,3S,5R)-5-(2-amino-6-mercapto-9H-purin-9-yl)-3-hydroxytetrahydrofuran-2-yl)methoxy)methyl) phosphonic acid

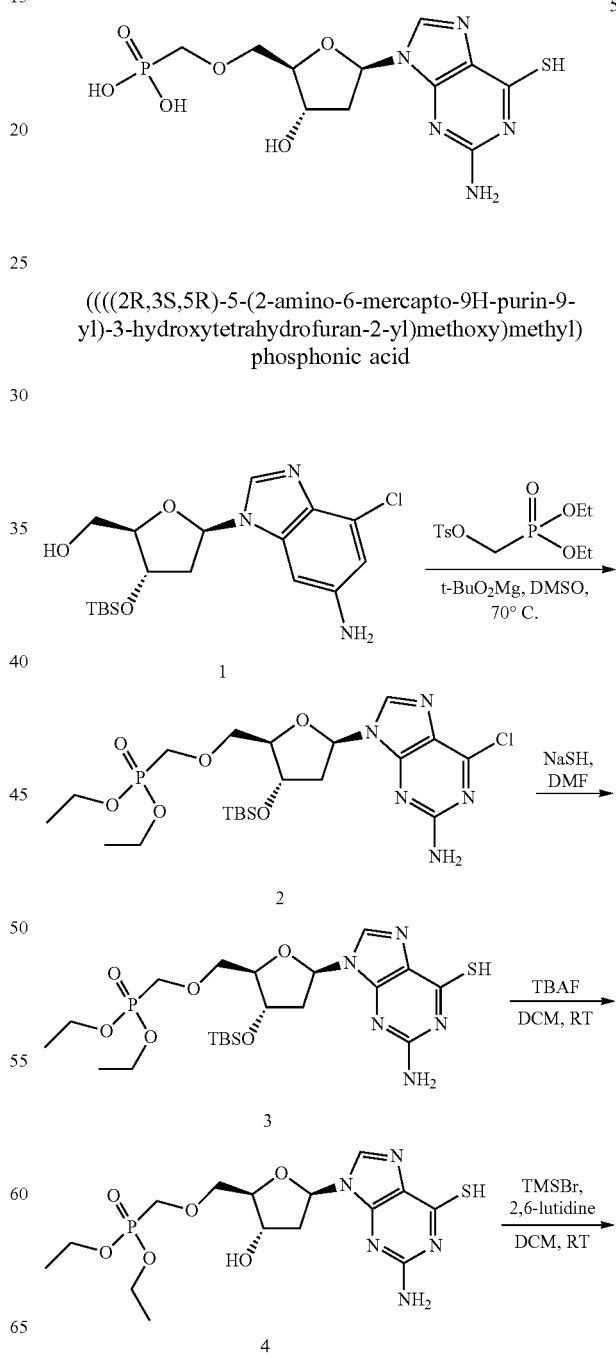

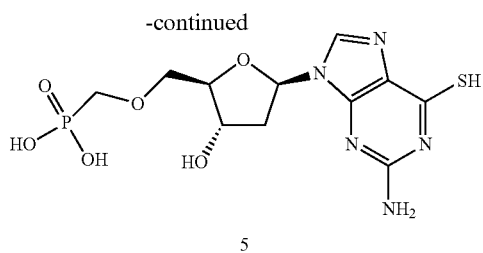

5

Step 1: diethyl ((((2R,3S,5R)-5-(2-amino-6-chloro-9H-purin-9-yl)-3-((tert-butyldimethylsilyl)oxy)tetrahydrofuran-2-yl)methoxy)methyl)phosphonate (2)

The mixture of 1 (685 mg, 1.71 mmol), (diethoxyphosphoryl)methyl 4-methylbenzenesulfonate (1.10 g, 3.43 mmol), t-BuO$_2$Mg (1.16 g, 6.84 mmol) in dry DMSO (20 mL) was stirred for 3 h at 70$_2$0 C. under positive Argon atmosphere. After cooling, the mixture was poured into cooled ammonium chloride solution (50 mL). The mixture was extracted with ethyl acetate (3×50 mL). Organic phase was combined, washed by brine (100 mL), dried over anhydrous sodium sulfate and filtered. The filtrate was concentrated under vacuum. The crude product was purified by column chromatography eluting with dichloromethane/methanol (50:1) to give 2 (660 mg, yield 69%).
LC-MS: (ES, m/z): [M+H]$^+$=551.1 $^1$H NMR (400 MHz, CDCl$_3$) δ 8.04 (s, 1H), 6.27 (dd, J=7.4, 6.3 Hz, 1H), 5.44 (s, 2H), 4.64-4.55 (m, 1H), 4.25-4.11 (m, 4H), 4.06 (dd, J=6.4, 3.6 Hz, 1H), 3.94 (dd, J=10.5, 4.2 Hz, 1H), 3.90-3.78 (m, 2H), 3.73 (dd, J=10.5, 3.6 Hz, 1H), 2.81 (ddd, J=13.2, 7.7, 5.7 Hz, 1H), 2.28 (ddd, J=13.1, 6.0, 2.8 Hz, 1H), 1.33 (dt, J=9.5, 7.1 Hz, 6H), 0.90 (s, 9H), 0.10 (d, J=6.1 Hz, 6H). $^{31}$P NMR (400 MHz, CDCl$_3$): δ 20.86.

Step 2: diethyl ((((2R,3S,5R)-5-(2-amino-6-mercapto-9H-purin-9-yl)-3-((tert-butyldimethylsilyl)oxy)tetrahydrofuran-2-yl)methoxy)methyl)phosphonate (3)

To a mixture of 2 (660 mg, 1.20 mmol) in dry DMF (10 mL) was added anhydrous NaHS (289 mg, 7.20 mmol) at 0° C. and the mixture was stirred for 2 hours. Then neutralized with aqueous 10% AcOH (2 mL). The resulting precipitate was filtered and dried under vacuum to give desired product 3 (320 mg, yield 58.7%).

LC-MS: (ES, m/z): [M+H]$^+$=548.1. $^1$H NMR (400 MHz, DMSO) δ 11.95 (s, 1H), 8.06 (s, 1H), 6.82 (s, 2H), 6.12 (t, J=6.9 Hz, 1H), 4.48 (s, 1H), 4.11-3.98 (m, 4H), 3.93 (s, 1H), 3.87 (d, J=8.1 Hz, 2H), 3.68 (ddd, J=45.8, 10.3, 4.7 Hz, 2H), 2.71-2.62 (m, 1H), 2.27-2.19 (m, 1H), 1.23 (td, J=6.9, 4.1 Hz, 6H), 0.88 (s, 9H), 0.10 (s, 6H). $^{31}$P NMR (400 MHz, DMSO): δ 21.23.

Step 3: Diethyl ((((2R,3S,5R)-5-(2-amino-6-mercapto-9H-purin-9-yl)-3-hydroxytetrahydrofuran-2-yl)methoxy)methyl)phosphonate (4)

To a solution of 3 (140 mg, 0.256 mmol) in dry THF (10 mL) was added dropwise TBAF (0.38 mL, 0.383 mmol) at ambient temperature and the mixture was stirred for 3 hours. The resulting mixture concentrated under vacuum at ambient temperature and purified by Prep-HPLC to give 4 (70 mg).
LC-MS: (ES, m/z): [M+H]$^+$=434.1. $^I$EINMR (400 MHz, DMSO) 6 7.64 (d, J=4.7 Hz, 1H), 6.12 (dd, J=7.9, 6.2 Hz, 1H), 5.31 (s, 1H), 5.23 (s, 2H), 4.37-4.25 (m, 1H), 4.10-3.97 (m, 4H), 3.87 (dd, J=9.8, 5.3 Hz, 3H), 3.74 (dd, J=10.5, 4.5 Hz, 1H), 3.63 (dd, J=10.5, 5.2 Hz, 1H), 2.64-2.54 (m, 1H), 2.12 (ddd, J=13.0, 6.0, 2.6 Hz, 1H), 1.23 (td, J=7.1, 3.7 Hz, 6H). $^{31}$P NMR (400 MHz, DMSO): δ 21.32.

Step 4: ((((2R,3S,5R)-5-(2-amino-6-mercapto-9H-purin-9-yl)-3-hydroxytetrahydrofuran-2-yl)methoxy)methyl)phosphonic acid (5)

To a mixture of 4 (50 mg, 0.115 mmol) and 2,6-lutidine (308 mg, 2.88 mmol) in dry DCM (5 mL) was added dropwise TMSBr (352 mg, 2.31 mmol) at ambient temperature and the mixture was stirred for overnight. The resulting mixture concentrated under vacuum and purified by Prep-HPLC to give 5 (5.0 mg, yield 10.2%). LC-MS: (ES, m/z): EM-Hr=376.1 $^1$H NMR (400 MHz, DMSO) δ 11.92 (s, 1H), 8.10 (s, 1H), 6.83 (s, 2H), 6.17-6.09 (m, 1H), 4.40-4.32 (m, 1H), 3.93 (d, J=2.3 Hz, 1H), 3.75 (dd, J=10.5, 4.5 Hz, 1H), 3.59 (d, J=8.5 Hz, 3H), 2.63 (dd, J=13.3, 7.8 Hz, 1H), 2.24-2.16 (m, 1H). $^{31}$P NMR (400 MHz, DMSO): δ 16.39.

EXAMPLES 15-32

The compounds in Table 2 can be prepared by the same method as described in Example 13 and 14.

TABLE 2

Compounds of Examples 15-32

| Ex. | Structure | MS | Name |
|---|---|---|---|
| 15 | 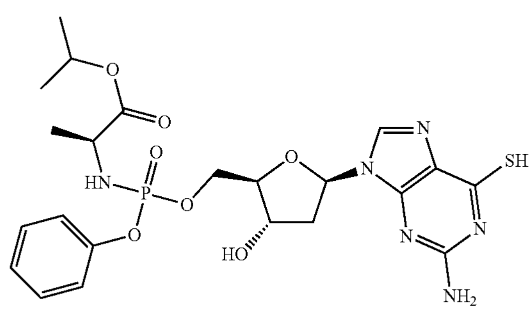 [SMILES: CC(C)OC(=O)[C@H](C)NP(=O)(OC[C@H]1O[C@@H](n2cnc3c(S)nc(N)nc32)C[C@@H]1O)Oc1ccccc1] | 552.16 | isopropyl ((((2R,3S,5R)-5-(2-amino-6-mercapto-9H-purin-9-yl)-3-hydroxytetrahydrofuran-2-yl)methoxy)(phenoxy)phosphoryl)-L-alaninate |

TABLE 2-continued

Compounds of Examples 15-32

| Ex. | Structure | MS | Name |
|---|---|---|---|
| 16 | 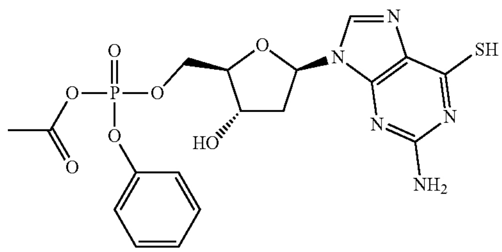 [SMILES: CC(=O)OP(=O)(OC[C@H]1O[C@@H](n2cnc3c(S)nc(N)nc32)C[C@@H]1O)Oc1ccccc1] | 481.08 | acetic (((2R,3S,5R)-5-(2-amino-6-mercapto-9H-purin-9-yl)-3-hydroxytetrahydrofuran-2-yl)methyl phenyl phosphoric) anhydride |
| 17 | 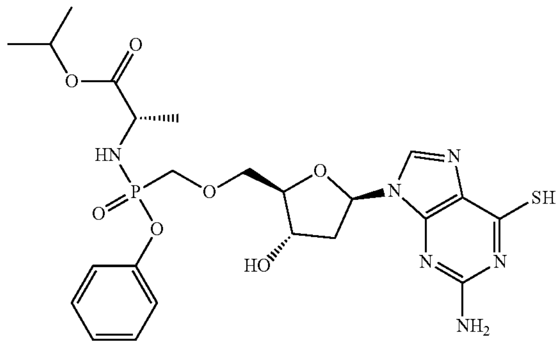 [SMILES: CC(C)OC(=O)[C@H](C)NP(=O)(COC[C@H]1O[C@@H](n2cnc3c(S)nc(N)nc32)C[C@@H]1O)Oc1ccccc1] | 566.17 | isopropyl (((((2R,3S,5R)-5-(2-amino-6-mercapto-9H-purin-9-yl)-3-hydroxytetrahydrofuran-2-yl)methoxy)methyl)(phenoxy)phosphoryl)-L-alaninate |
| 18 | 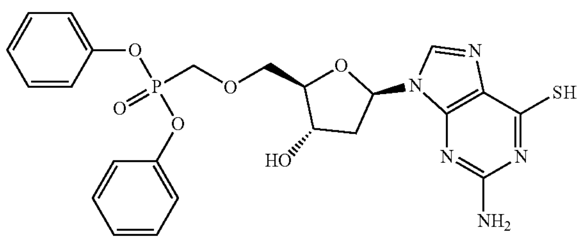 [SMILES: Nc1nc(S)c2ncn([C@H]3C[C@H](O)[C@@H](COCP(=O)(Oc4ccccc4)Oc4ccccc4)O3)c2n1] | 529.12 | diphenyl ((((2R,3S,5R)-5-(2-amino-6-mercapto-9H-purin-9-yl)-3-hydroxytetrahydrofuran-2-yl)methoxy)methyl)phosphonate |
| 19 | 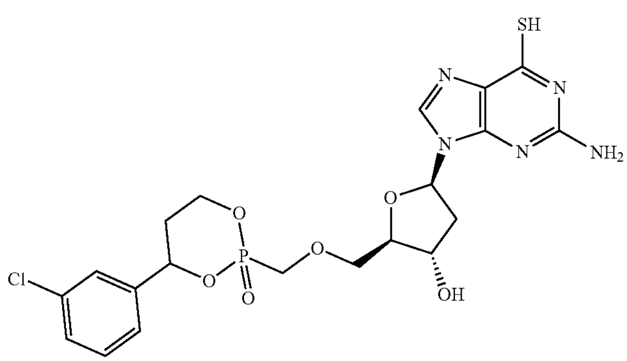 [SMILES: Nc1nc(S)c2ncn([C@H]3C[C@H](O)[C@@H](COCP4(=O)OCCC(c5cccc(Cl)c5)O4)O3)c2n1] | 527.08 | 2-((((2R,3S,5R)-5-(2-amino-6-mercapto-9H-purin-9-yl)-3-hydroxytetrahydrofuran-2-yl)methoxy)methyl)-4-(3-chlorophenyl)-1,3,2-dioxaphosphinane 2-oxide |
| 20 | 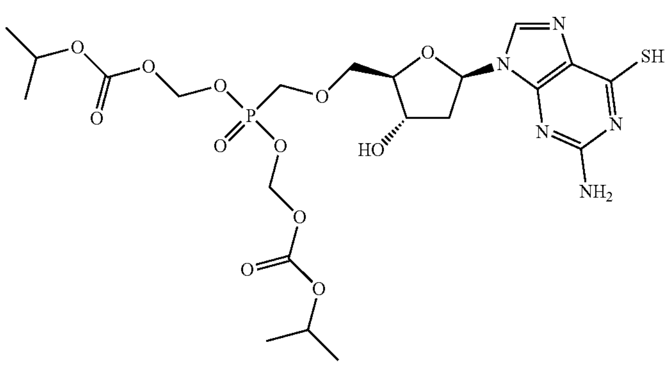 [SMILES: CC(C)OC(=O)OCOP(=O)(COC[C@H]1O[C@@H](n2cnc3c(S)nc(N)nc32)C[C@@H]1O)OCOC(=O)OC(C)C] | 609.15 | ((((((2R,3S,5R)-5-(2-amino-6-mercapto-9H-purin-9-yl)-3-hydroxytetrahydrofuran-2-yl)methoxy)methyl)phosphoryl)bis(oxy))bis(methylene) diisopropyl bis(carbonate) |

TABLE 2-continued

Compounds of Examples 15-32

| Ex. | Structure | MS | Name |
|---|---|---|---|
| 21 | 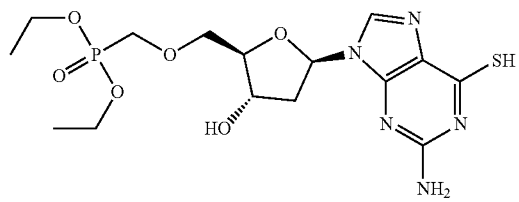 [SMILES: CCOP(=O)(COC[C@H]1O[C@@H](n2cnc3c(S)nc(N)nc32)C[C@@H]1O)OCC] | 433.12 | diethyl ((((2R,3S,5R)-5-(2-amino-6-mercapto-9H-purin-9-yl)-3-hydroxytetrahydrofuran-2-yl)methoxy)methyl)phosphonate |
| 22 | 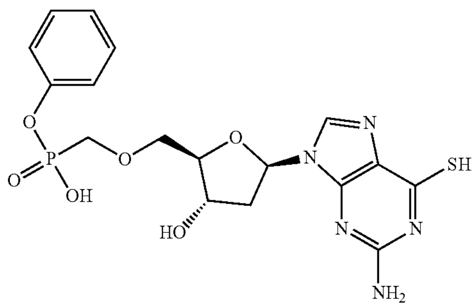 [SMILES: Nc1nc(S)c2ncn([C@H]3C[C@H](O)[C@@H](COCP(=O)(O)Oc4ccccc4)O3)c2n1] | 453.09 | phenyl hydrogen ((((2R,3S,5R)-5-(2-amino-6-mercapto-9H-purin-9-yl)-3-hydroxytetrahydrofuran-2-yl)methoxy)methyl)phosphonate |
| 23 | 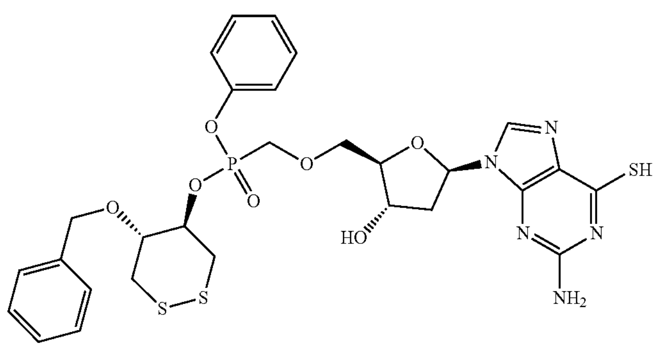 [SMILES: Nc1nc(S)c2ncn([C@H]3C[C@H](O)[C@@H](COCP(=O)(Oc4ccccc4)O[C@H]4CSSC[C@@H]4OCc4ccccc4)O3)c2n1] | 677.12 | (4R,5R)-5-(benzyloxy)-1,2-dithian-4-yl phenyl ((((2R,3S,5R)-5-(2-amino-6-mercapto-9H-purin-9-yl)-3-hydroxytetrahydrofuran-2-yl)methoxy)methyl) phosphonate |
| 24 | 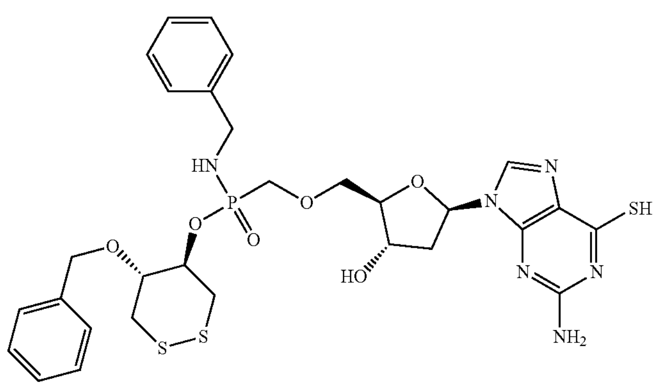 [SMILES: Nc1nc(S)c2ncn([C@H]3C[C@H](O)[C@@H](COCP(=O)(NCc4ccccc4)O[C@H]4CSSC[C@@H]4OCc4ccccc4)O3)c2n1] | 690.15 | (4R,5R)-5-(benzyloxy)-1,2-dithian-4-yl P-((((2R,3S,5R)-5-(2-amino-6-mercapto-9H-purin-9-yl)-3-hydroxytetrahydrofuran-2-yl)methoxy)methyl)-N-benzylphosphonamidate |

TABLE 2-continued

Compounds of Examples 15-32

| Ex. | Structure | MS | Name |
|---|---|---|---|
| 25 | 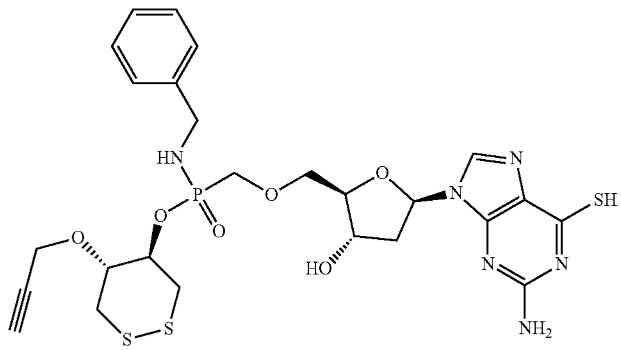 [SMILES: C#CCO[C@H]1CSSC[C@@H]1OP(=O)(COC[C@H]1O[C@@H](n2cnc3c(S)nc(N)nc32)C[C@@H]1O)NCc1ccccc1] | 638.12 | (4R,5R)-5-(prop-2-yn-1-yloxy)-1,2-dithian-4-yl P-((((2R,3S,5R)-5-(2-amino-6-mercapto-9H-purin-9-yl)-3-hydroxytetrahydrofuran-2-yl)methoxy)methyl)-N-benzylphosphonamidate |
| 26 | 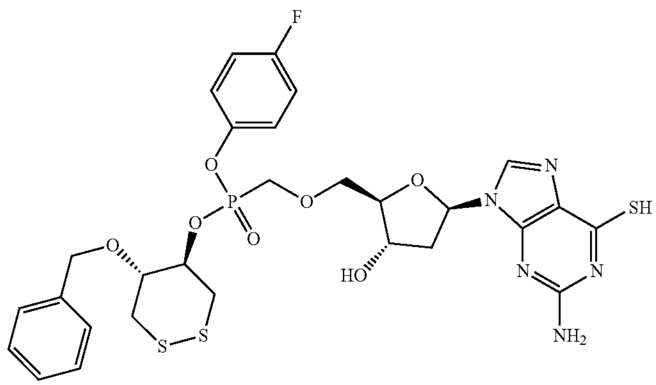 [SMILES: Nc1nc(S)c2ncn([C@H]3C[C@H](O)[C@@H](COCP(=O)(Oc4ccc(F)cc4)O[C@H]4CSSC[C@@H]4OCc4ccccc4)O3)c2n1] | 695.11 | (4R,5R)-5-(benzyloxy)-1,2-dithian-4-yl (4-fluorophenyl) ((((2R,3S,5R)-5-(2-amino-6-mercapto-9H-purin-9-yl)-3-hydroxytetrahydrofuran-2-yl)methoxy)methyl)phosphonate |
| 27 | 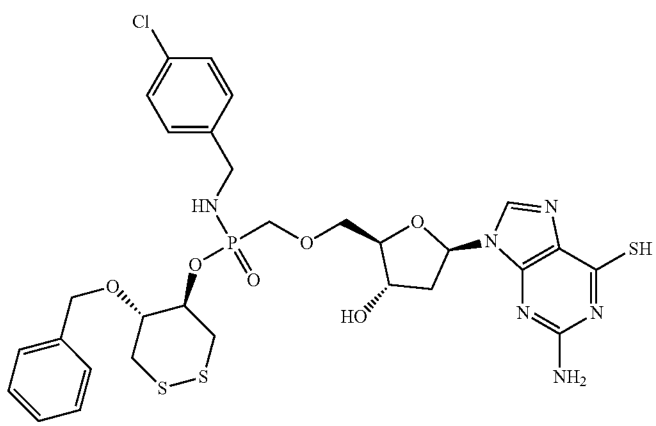 [SMILES: Nc1nc(S)c2ncn([C@H]3C[C@H](O)[C@@H](COCP(=O)(NCc4ccc(Cl)cc4)O[C@H]4CSSC[C@@H]4OCc4ccccc4)O3)c2n1] | 711.08 | (4R,5R)-5-(benzyloxy)-1,2-dithian-4-yl (3-chlorophenyl) ((((2R,3S,5R)-5-(2-amino-6-mercapto-9H-purin-9-yl)-3-hydroxytetrahydrofuran-2-yl)methoxy)methyl)phosphonate |
| 28 | 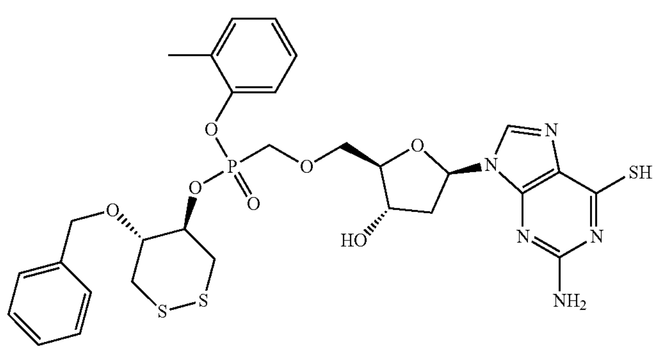 [SMILES: Cc1ccccc1OP(=O)(COC[C@H]1O[C@@H](n2cnc3c(S)nc(N)nc32)C[C@@H]1O)O[C@H]1CSSC[C@@H]1OCc1ccccc1] | 691.14 | (4R,5R)-5-(benzyloxy)-1,2-dithian-4-yl o-tolyl ((((2R,3S,5R)-5-(2-amino-6-mercapto-9H-purin-9-yl)-3-hydroxytetrahydrofuran-2-yl)methoxy)methyl)phosphonate |

TABLE 2-continued

Compounds of Examples 15-32

| Ex. | Structure | MS | Name |
|---|---|---|---|
| 29 | 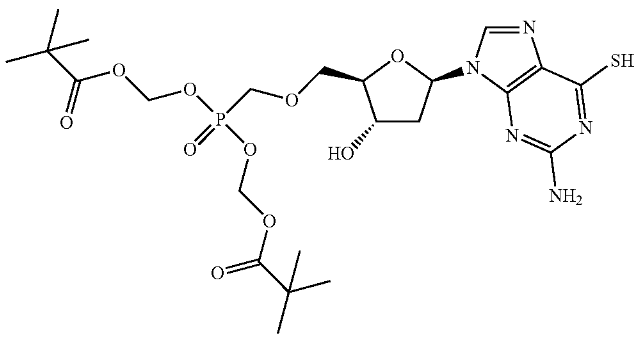 [SMILES: CC(C)(C)C(=O)OCOP(=O)(COC[C@H]1O[C@@H](n2cnc3c(S)nc(N)nc32)C[C@@H]1O)OCOC(=O)C(C)(C)C] | 605.60 | ((((((2R,3S,5R)-5-(2-amino-6-mercapto-9H-purin-9-yl)-3-hydroxytetrahydrofuran-2-yl)methoxy)methyl)phosphoryl)bis(oxy))bis(methylene) bis(2,2-dimethylpropanoate) |
| 30 | 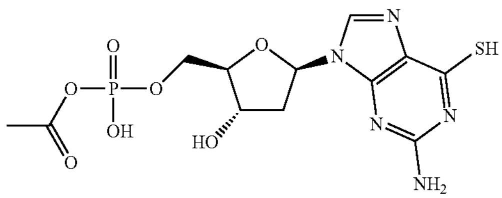 [SMILES: CC(=O)OP(=O)(O)OC[C@H]1O[C@@H](n2cnc3c(S)nc(N)nc32)C[C@@H]1O] | 405.05 | acetic (((2R,3S,5R)-5-(2-amino-6-mercapto-9H-purin-9-yl)-3-hydroxytetrahydrofuran-2-yl)methyl phosphoric) anhydride |
| 31 | 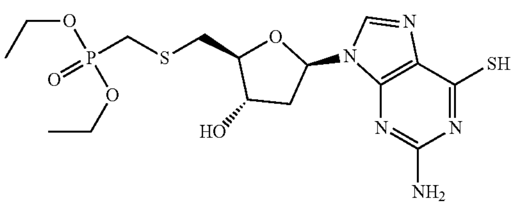 [SMILES: CCOP(=O)(CSC[C@H]1O[C@@H](n2cnc3c(S)nc(N)nc32)C[C@@H]1O)OCC] | 449.10 | diethyl (((((2S,3S,5R)-5-(2-amino-6-mercapto-9H-purin-9-yl)-3-hydroxytetrahydrofuran-2-yl)methyl)thio)methyl)phosphona |

EXAMPLE 32

The compounds of Examples 1-31 are tested Xenograft animal models with A549 cells with oral dose at 5 mg/kg for 21 days. 6-thio-dG is used as control. The compounds of the Examples 1-31 show good efficacy against tumor growth. More importantly, these compounds have much less toxicity than 6-thio-dG. These compounds can be used to treat various diseases, such as cancer and viral infections While the invention has been described and illustrated in reference to specific embodiments thereof, those skilled in the art will appreciate that various changes, modifications, and substitutions can be made therein without departing from the spirit and scope of the invention. For example, effective dosages other than the preferred doses as set forth hereinabove may be applicable as a consequence of variations in the responsiveness of the human being treated for cancer or others. Likewise, the pharmacologic response observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended therefore that the invention be limited only by the scope of the claims which follow and that such claims be interpreted as broadly as is reasonable.

What is claimed is:

1. A compound having the following formula (I), or a tautomer thereof:

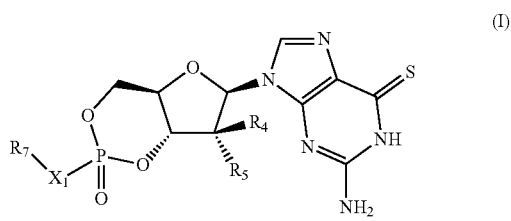

wherein $X_1$ is —O— or —NH—;

$R_7$ is alkyl, alkyl substituted with one or more —OH or halo groups, alkenyl, alkenyl substituted with one or more —OH or halo groups, alkynyl, alkynyl substituted with one or more —OH or halo groups, cycloalkyl, cycloalkyl substituted with one or more —OH or halo groups, aryl, aryl substituted with one or more —OH, halo, —CN, —NO$_2$, alkyl, alkoxy, or haloalkyl groups, benzyl, benzyl substituted with one or more —OH, halo, —CN, —NO$_2$, alkyl, alkoxy, or haloalkyl groups, heteroaryl, heteroaryl substituted with one or more —OH, halo, —CN, —NO$_2$, alkyl, alkoxy, or haloalkyl groups, heterocyclyl, heterocyclic substituted with one or more —OH, halo, —CN, —NO$_2$, alkyl, alkoxy, or haloalkyl groups, —CH(CH$_3$)COOCH(CH$_3$)$_2$

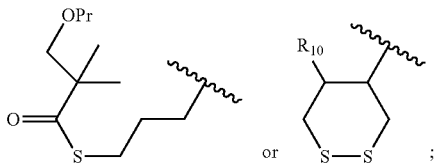

R$_4$ is —H, —OH, —CH$_3$, —Cl, —F, —N$_3$, —OCH$_3$, alkenyl, or alkynyl;

R$_5$ is —H, —OH, —CH$_3$, -Cl, —F, —N$_3$, —OCH$_3$, alkenyl, or alkynyl; and

R$_{10}$ is —L—M, wherein L is —O—, —O—CH$_2$—, —S—, —NH—, —CO—, —SO—, or —CH$_2$—, and M is alkyl, alkyl substituted with one or more —OH or halo groups, alkenyl, alkenyl substituted with one or more —OH or halo groups, alkynyl, alkynyl substituted with one or more -OH or halo groups, alkoxy, alkoxy substituted with one or more —OH or halo groups, cycloalkyl, cycloalkyl substituted with one or more —OH or halo groups, aryl, aryl substituted with one or more —OH, halo, —CN, —NO$_2$, alkyl, alkoxy, or haloalkyl groups, benzyl, benzyl substituted with one or more —OH, halo, —CN, —NO$_2$, alkyl, alkoxy, or haloalkyl groups, heteroaryl, heteroaryl substituted with one or more —OH, halo, —CN, —NO$_2$, alkyl, alkoxy, or haloalkyl groups, heterocyclyl, or heterocyclic substituted with one or more —OH, halo, —CN, —NO$_2$, alkyl, alkoxy, or haloalkyl groups.

2. The compound of claim 1, wherein X$_1$ is —O—; R$_7$ is

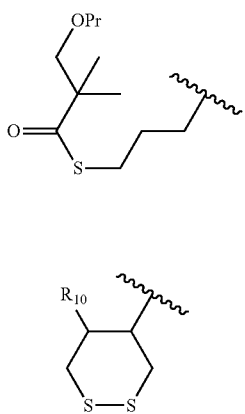

R$_4$ is —H;

R$_5$ is —H; and

R$_{10}$ is —L—M, wherein L is —O— or —O—CH$_2$—, and M is alkynyl, alkynyl substituted with one or more —OH or halo groups, aryl, aryl substituted with one or more —OH, halo, —CN, —NO$_2$, alkyl, alkoxy, or haloalkyl groups, benzyl, benzyl substituted with one or more —OH, halo, —CN, —NO$_2$, alkyl, alkoxy, or haloalkyl groups, heterocyclyl, or heterocyclic substituted with one or more —OH, halo, —CN, —NO$_2$, alkyl, alkoxy, or haloalkyl groups.

3. The compound of claim 2, wherein the compound is selected from the group consisting of: 2-amino-9-((2S,4aR,6R,7aS)-2-(((4R, 5R)-5-(benzyloxy)- 1,2-dithian-4-yl)oxy)-2-oxidotetrahydro-4H-furo[3,2-d][1,3,2]dioxaphosphinin-6-yl)- 1, 9-dihydro-6H-purine-6-thione; 2-amino-9-((2S, 4aR,6R,7aS)-2-(((4S, 5S)-5-(benzyloxy)- 1,2-dithian-4-yl)oxy)-2-oxidotetrahydro-4H-furo[3,2-d][1,3,2]dioxaphosphinin-6-yl)- 1,9-dihydro-6H-purine-6-thione; 2-amino-9-((2R,4aR,6R,7aS)-2-(((4S,5S)-5-(benzyloxy)-1,2-dithian-4-yl)oxy)-2-oxidotetrahydro-4H-furo[3,2-d][1,3,2]dioxaphosphinin-6-yl)-1,9-dihydro-6H-purine-6-thione; 2-amino-9-((2R,4aR,6R,7aS)-2-(((4R,5R)-5-(benzyloxy)-1,2-dithian-4-yl)oxy)-2-oxidotetrahydro-4H-furo[3,2-d][1,3,2]dioxaphosphinin-6-yl)-1,9-dihydro-6H-purine-6-thione; S-(3-(((2R,4aR,6R,7aS)-6-(2-amino-6-thioxo-1,6-dihydro-9H-purin-9-yl)-2-oxidotetrahydro-4H-furo[3,2-d][1,3,2]dioxaphosphinin-2-yl)oxy)propyl) 2,2-dimethyl-3-propoxypropanethioate; S-(3-(((2S,4aR,6R,7aS)-6-(2-amino-6-thioxo-1,6-dihydro-9H-purin-9-yl)-2-oxidotetrahydro-4H-furo[3,2-d][1,3,2]dioxaphosphinin-2-yl)oxy)propyl) 2,2-dimethyl-3-propoxypropanethioate; 2-amino-9-((2S,4aR,6R,7aS)-2-(((4R,5R)-5-(benzyloxy)-1,2-dithian-4-yl)oxy)-2-sulfidotetrahydro-4H-furo[3,2-d][1,3,2]dioxaphosphinin-6-yl)-1,9-dihydro-6H-purine-6-thione;

2-amino-9-((2R,4aR,6R,7aS)-2-(((4R,5R)-5-((2-methylbenzyl)oxy)-1,2-dithian-4-yl)oxy)-2- oxidotetrahydro-4H-furo[3,2-d][1,3,2]dioxaphosphinin-6-yl)-1,9-dihydro-6H-purine-6-thione; 2- amino-9-((2R,4aR,6R,7aS)-2-oxido-2-(((4R,5R)-5-(prop-2-yn-l-yloxy)-1,2-dithian-4- yl)oxy)tetrahydro-4H-furo[3,2-d][1,3,2]dioxaphosphinin-6-yl)-1,9-dihydro-6H-purine-6-thione; 2-amino-9-((2R,4aR,6R,7aS)-2-(((4R,5R)-5-methoxy-1,2-dithian-4-yl)oxy)-2-oxidotetrahydro-4H-furo[3,2-d][1,3,2]dioxaphosphinin-6-yl)-1,9-dihydro-6H-purine-6-thione; and 2-amino-9-((2R,4aR,6R,7aS)-2-oxido-2-(((4R,5R)-5-(pyridin-4-ylmethoxy)-1,2-dithian-4-yl)oxy)tetrahydro-4H-furo[3,2-d][1,3,2]dioxaphosphinin-6-yl)-1,9-dihydro-6H-purine-6-thione.

4. A compound having the following formula (II), or a tautomer thereof: or a pharmaceutical acceptable solvate thereof,

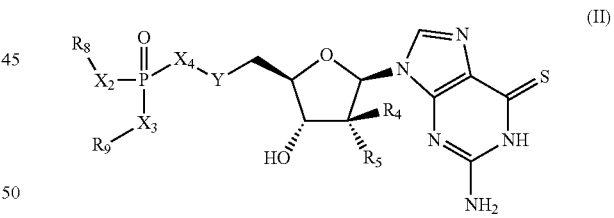

(II)

wherein

X$_2$ is —O— or —NH—;

X$_3$ is —O— or —NH—;

X$_4$ is —CH$_2$— or nil;

Y is —O—, —S—, or —SO$_2$—;

R$_8$ and R$_9$ are independently selected from the group consisting of alkyl, alkyl substituted with one or more —OH or halo groups, alkenyl, alkenyl substituted with one or more —OH or halo groups, alkynyl, alkynyl substituted with one or more —OH or halo groups, cycloalkyl, cycloalkyl substituted with one or more —OH or halo groups, aryl, aryl substituted with one or more —OH, halo, —CN, —NO$_2$, alkyl, alkoxy, or haloalkyl groups, benzyl, benzyl substituted with one or more —OH, halo, —CN, —NO$_2$, alkyl, alkoxy, or haloalkyl groups, heteroaryl, heteroaryl substituted with one or more —OH, halo, —CN, —NO$_2$, alkyl, alkoxy, or haloalkyl groups, heterocyclyl, heterocyclic substituted with one or more —OH, halo, —CN, —NO$_2$, alkyl, alkoxy, or haloalkyl groups, —CH(CH$_3$)COOCH(CH$_3$)

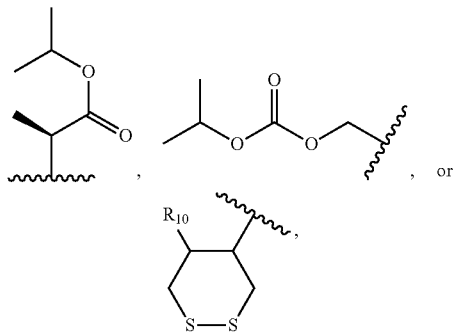

or R$_8$ and R$_9$ form a five-membered or six-membered heterocyclo ring or a five-membered or six-membered heterocyclo ring substituted with one or more —OH, halo, —CN, —NO$_2$, alkyl, alkoxy, benzyl, benzyl substituted with one or more —OH, halo, —CN, —NO$_2$, alkyl, alkoxy, or haloalkyl groups, or haloalkyl groups;

R$_4$ is —H, —OH, —CH$_3$, —Cl, —F, —N$_3$, —OCH$_3$, alkenyl, or alkynyl;

R$_5$ is —H, —OH, —CH$_3$, —Cl, —F, —N$_3$, —OCH$_3$, alkenyl, or alkynyl; and

R$_{10}$ is —L—M, wherein L is —O—, —O—CH$_2$—, —S—, —NH—, —CO—, —SO—, or —CH$_2$—, and M is alkyl, alkyl substituted with one or more —OH or halo groups, alkenyl, alkenyl substituted with one or more —OH or halo groups, alkynyl, alkynyl substituted with one or more —OH or halo groups, alkoxy, alkoxy substituted with one or more —OH or halo groups, cycloalkyl, cycloalkyl substituted with one or more —OH or halo groups, aryl, aryl substituted with one or more —OH, halo, —CN, —NO$_2$, alkyl, alkoxy, or haloalkyl groups, benzyl, benzyl substituted with one or more —OH, halo, —CN, —NO$_2$, alkyl, alkoxy, or haloalkyl groups, heteroaryl, heteroaryl substituted with one or more —OH, halo, —CN, —NO$_2$, alkyl, alkoxy, or haloalkyl groups, heterocyclyl, or heterocyclic substituted with one or more —OH, halo, —CN, —NO$_2$, alkyl, alkoxy, or haloalkyl groups.

5. The compound of claim 4, wherein

R$_8$ and R$_9$ are independently selected from the group consisting of alkyl, alkyl substituted with one or more —OH or halo groups, aryl, aryl substituted with one or more —OH, halo, —CN, —NO$_2$, alkyl, alkoxy, or haloalkyl groups, benzyl, benzyl substituted with one or more —OH, halo, —CN, —NO$_2$, alkyl, alkoxy, or haloalkyl groups, —CH(CH$_3$)COOCH(CH$_3$)$_2$, —COCH$_3$,

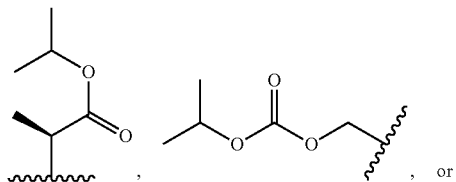

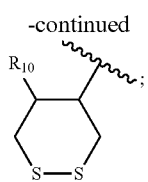

R$_4$ is —H;

R$_5$ is —H; and

R$_{10}$ is —L—M, wherein L is —O— or —O—CH$_2$—, and M is alkynyl, alkynyl substituted with one or more —OH or halo groups, aryl, aryl substituted with one or more —OH, halo, —CN, —NO$_2$, alkyl, alkoxy, or haloalkyl groups, benzyl, benzyl substituted with one or more —OH, halo, —CN, —NO$_2$, alkyl, alkoxy, or haloalkyl groups, heteroaryl, or heteroaryl substituted with one or more —OH, halo, —CN, —NO$_2$, alkyl, alkoxy, or haloalkyl groups.

6. The compound of claim 4, wherein

R$_8$ and R$_9$ form a five-membered or six-membered heterocyclo ring or a five-membered or six-membered heterocyclo ring substituted with one or more —OH, halo, —CN, —NO$_2$, alkyl, alkoxy, benzyl, benzyl substituted with one or more —OH, halo, —CN, —NO$_2$, alkyl, alkoxy, or haloalkyl groups, or haloalkyl groups;

R$_4$ is —H; and

R$_5$ is —H.

7. The compound of claim 4, wherein the compound is selected from the group consisting of: isopropyl ((((2R,3S,5R)-5-(2-amino-6-mercapto-9H-purin-9-yl)-3-hydroxytetrahydrofuran-2-yl)methoxy)(phenoxy)phosphoryl)-L-alaninate; acetic (((2R,3S,5R)-5-(2-amino-6-mercapto-9H-purin-9-yl)-3-hydroxytetrahydrofuran-2-yl)methyl phenyl phosphoric) anhydride; isopropyl (((((2R,3S,5R)-5-(2-amino-6-mercapto-9H-purin-9-yl)-3-hydroxytetrahydrofuran-2-yl)methoxy)methyl)(phenoxy)phosphoryl) -L-alaninate; diphenyl ((((2R,3S,5R)-5-(2-amino-6-mercapto-9H-purin-9-yl)-3-hydroxytetrahydrofuran-2-yl)methoxy)methyl)phosphonate; 2-((((2R,3S,5R)-5-(2-amino-6-mercapto-9H-purin-9-yl)-3-hydroxytetrahydrofuran-2-yl)methoxy)methyl)-4-(3-chlorophenyl)-1,3,2-dioxaphosphinane 2-oxide; ((((((2R,3S,5R)-5-(2-amino-6-mercapto-9H-purin-9-yl)-3-hydroxytetrahydrofuran-2-yl)methoxy)methyl)phosphoryl)bis(oxy))bis(methylene) diisopropyl bis(carbonate); diethyl ((((2R,3S,5R)-5-(2-amino-6-mercapto-9H-purin-9-yl)-3-hydroxytetrahydrofuran-2-yl)methoxy)methyl)phosphonate; ((((2R,3S,5R)-5-(2-amino-6-mercapto-9H-purin-9-yl)-3-hydroxytetrahydrofuran-2-yl)methoxy)methyl)phosphonic acid; phenyl hydrogen ((((2R,3S,5R) -5-(2-amino-6-mercapto-9H-purin-9-yl)-3-hydroxytetrahydrofuran-2-yl)methoxy)methyl)phosphonate; (4R,5R)-5-(benzyloxy)-1,2-dithian-4-yl phenyl ((((2R,3S,5R) -5-(2-amino-6-mercapto-9H-purin-9-yl)-3-hydroxytetrahydrofuran-2-yl)methoxy)methyl)phosphonate; (4R,5R)-5-(benzyloxy)-1,2-dithian-4-yl P-((((2R,3S,5R) -5 -(2-amino-6-mercapto-9H-purin-9-yl)-3-hydroxytetrahydrofuran-2-yl)methoxy)methyl)-N-benzylphosphonamidate; (4R, 5R)-5 -(prop-2-yn-1-yloxy)-1,2-dithian-4-yl P-((((2R,3S,5R) -5 -(2-amino-6-mercapto-9H-purin-9-yl)-3-hydroxytetrahydrofuran-2-yl)methoxy)methyl)-N-benzylphosphonamidate; (4R,5R)-5-(benzyloxy)-1,2-dithian-4-yl (4-fluorophenyl) ((((2R,3S,5R) -5 -(2-amino-6-mercapto-9H-purin-9-yl)-3 -hydroxytetrahydrofuran-2-yl)methoxy)methyl)phosphonate; (4R,5R)-5-

(benzyloxy)-1,2-dithian-4-yl (4-fluorophenyl) ((((2R,3S,5R)-5-(2-amino-6-mercapto-9H-purin-9-yl)-3-hydroxytetrahydrofuran-2-yl)methoxy)methyl)phosphonate; (4R,5R)-5-(benzyloxy)-1,2-dithian-4-yl (3-chlorophenyl) ((((2R,3S,5R)-5-(2-amino-6-mercapto-9H-purin-9-yl)-3-hydroxytetrahydrofuran-2-yl)methoxy)methyl)phosphonate; (4R,5R)-5-(benzyloxy)-1,2-dithian-4-yl o-tolyl ((((2R,3S,5R)-5-(2-amino-6-mercapto-9H-purin-9-yl)-3-hydroxytetrahydrofuran-2-yl)methoxy)methyl) phosphonate; ((((((2R,3S,5R)-5-(2-amino-6-mercapto-9H-purin-9-yl)-3-hydroxytetrahydrofuran-2-yl)methoxy)methyl)phosphoryl)bis(oxy))bis(methylene) bis(2,2-dimethylpropanoate); acetic ((((2R,3S,5R)-5-(2-amino-6-mercapto-9H-purin-9-yl)-3-hydroxytetrahydrofuran-2-yl)methyl phosphoric) anhydride; and diethyl (((((2S,3S,5R)-5-(2-amino-6-mercapto-9H-purin-9-yl)-3-hydroxytetrahydrofuran-2-yl)methyl)thio)methyl)phosphonate.

\* \* \* \* \*